United States Patent
Adachi et al.

(10) Patent No.: US 9,985,215 B2
(45) Date of Patent: May 29, 2018

(54) LIGHT-EMITTING MATERIAL, AND ORGANIC LIGHT-EMITTING ELEMENT

(71) Applicant: KYUSHU UNIVERSITY NATIONAL UNIVERSITY CORPORATION, Fukuoka-shi, Fukuoka (JP)

(72) Inventors: Chihaya Adachi, Fukuoka (JP); Tetsuya Nakagawa, Fukuoka (JP); Jie Li, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 887 days.

(21) Appl. No.: 14/383,971

(22) PCT Filed: Mar. 7, 2013

(86) PCT No.: PCT/JP2013/056245
§ 371 (c)(1),
(2) Date: Sep. 9, 2014

(87) PCT Pub. No.: WO2013/133359
PCT Pub. Date: Sep. 12, 2013

(65) Prior Publication Data
US 2015/0048338 A1    Feb. 19, 2015

(30) Foreign Application Priority Data
Mar. 9, 2012    (JP) ................................ 2012-053437

(51) Int. Cl.
*H01L 51/50*    (2006.01)
*H01L 51/00*    (2006.01)
(Continued)

(52) U.S. Cl.
CPC ........ *H01L 51/0061* (2013.01); *C07D 487/16* (2013.01); *C09K 11/06* (2013.01);
(Continued)

(58) Field of Classification Search
CPC combination set(s) only.
See application file for complete search history.

(56) References Cited

U.S. PATENT DOCUMENTS

2011/0297925 A1    12/2011    Breuning
2012/0091884 A1    7/2012    MacDonald et al.

FOREIGN PATENT DOCUMENTS

CN    101223174 A    7/2008
CN    102317408 A    1/2012
(Continued)

OTHER PUBLICATIONS

Japanese Office Action dated Aug. 10, 2016 in corresponding Japanese Patent appl. No. 2014-503534 with English translation of excerpts from Japanese original.
(Continued)

*Primary Examiner* — Jennifer A Chriss
*Assistant Examiner* — Sean M DeGuire
(74) *Attorney, Agent, or Firm* — Browdy and Neimark, PLLC

(57) ABSTRACT

The compound represented by the following general formula is useful as a light-emitting material for an organic light-emitting device. $Z^1$, $Z^2$ and $Z^3$ in the following general formula each independently represent a substituent.

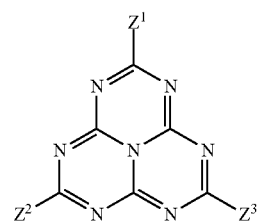

7 Claims, 5 Drawing Sheets

(51) Int. Cl.
*C07D 487/16* (2006.01)
*C09K 11/06* (2006.01)

(52) U.S. Cl.
CPC ............ *C09K 2211/1007* (2013.01); *C09K 2211/1014* (2013.01); *C09K 2211/1074* (2013.01); *H01L 51/0067* (2013.01); *H01L 51/0072* (2013.01); *H01L 51/5012* (2013.01)

(56) References Cited

FOREIGN PATENT DOCUMENTS

| | | |
|---|---|---|
| JP | 2004-182737 A | 7/2004 |
| JP | 2000-506916 A | 6/2006 |
| JP | 2006267981 A | 10/2006 |
| WO | 97/33323 A | 9/1997 |
| WO | 2007006807 A1 | 1/2007 |
| WO | 2008083974 A1 | 7/2008 |
| WO | 2008083975 A1 | 7/2008 |
| WO | 2010000614 A1 | 1/2010 |
| WO | 2010094378 A1 | 8/2010 |
| WO | 2010132953 A1 | 11/2010 |

OTHER PUBLICATIONS

Chinese Office Action dated Apr. 10, 2015 in corresponding Chinese Patent appl. No. 201380013353.9 with English translation.

Kroke, E. et al "Alkalicyamelurates, $M_3[C_6N_7O_3]$-$xH_2O$, M = Li, Na, K, Rb, Cs:UV-luminescent and thermally very stable ionic tri-s-triazine derivatives†" Dalton Trans. 3900-3908 (Aug. 2004).

Traber, B. et al "Donor-Substituted Heptaazaphenalene as a Nonlinear Optically Active Molecule with Multiple Charge-Transfer Transitions[‡]" Eur. J. Org. Chem. 4387-4390 (2004).

Zheng, W. et al "Theroretical Study of 1,3,4,6,7,9,9b-Heptaazaphenalene and Its Ten Derivatives" J. Phys. Chem. A 108:97-706 (2004).

International search report, dated Jun. 13, 2014. Application No. 2013056245.

International preliminary report, dated Sep. 12, 2014. Application No. 2013056245.

LIGHT-EMITTING MATERIAL, AND ORGANIC LIGHT-EMITTING ELEMENT

TECHNICAL FIELD

The present invention relates to a light-emitting material having a heptaazaphenalene structure, and an organic light-emitting device, such as an organic electroluminescent device (organic EL device), using the light-emitting material.

BACKGROUND ART

Compounds having a heptaazaphenalene structure and their use have been variously studied. For example, it has been found that a compound having a heptaazaphenalene structure is useful as an ultraviolet ray absorbent and may be applied to cosmetics and medical drugs (see, for example, PTLs 1 to 3).

The application of a compound having a heptaazaphenalene structure to an organic light-emitting device has not been studied for a long time. In recent years, however, it has been found that a compound having a heptaazaphenalene structure is useful as a hole injection material (see PTL 4).

CITATION LIST

Patent Literatures

PTL 1: WO 2008/83974
PTL 2: WO 2008/83975
PTL 3: WO 2007/6807
PTL 4: WO 2010/614

SUMMARY OF INVENTION

Technical Problem

As described above, a compound having a heptaazaphenalene structure has been variously studied, and a slight proposal for application thereof to an organic electroluminescent device has also been made. However, all the compounds having a heptaazaphenalene structure have not yet been entirely studied. In particular, there is no literature found that confirms specific usefulness of a compound having a heptaazaphenalene structure as a light-emitting material of an organic electroluminescent device. Furthermore, there is no literature found that discusses the relationship between the chemical structure of a compound having a heptaazaphenalene structure and the usefulness of the compound as a light-emitting material. Accordingly, it is currently difficult to estimate the usefulness as a light-emitting material based on the chemical structure. In consideration of the problems, the present inventors have studied the usefulness as a light-emitting material of a compound having a heptaazaphenalene structure, and have further studied for obtaining useful knowledge. The inventors have also earnestly studied for providing a general formula of a compound that is useful as a light-emitting material to generalize a useful light-emitting material.

Solution to Problem

As a result of earnest investigations for achieving the aforementioned objects, the inventors have found that a particular compound having a heptaazaphenalene structure is useful as a light-emitting material of an organic light-emitting device. In particular, the inventors have firstly found a compound that is useful as a delayed fluorescent material and a compound that has an extremely high light emission efficiency in compounds having a heptaazaphenalene structure, and have clarified that an excellent organic light-emitting device that has not been proposed may be provided inexpensively. Light emission efficiency is defined and hereafter used for mean photoluminescence quantum efficiency, electroluminescence quantum efficiency, or both as appropriate. Based on the knowledge, the inventors thus provide the invention described hereinbelow as a measure for solving the problems.

(1) A light-emitting material containing a compound represented by the following general formula (1):

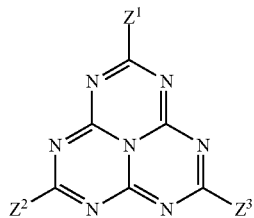

General Formula (1)

wherein in the general formula (1), $Z^1$, $Z^2$ and $Z^3$ each independently represent a substituent.

(2) The light-emitting material according to the item (1), wherein $Z^1$, $Z^2$ and $Z^3$ in the general formula (1) are the same as each other.

(3) The light-emitting material according to the item (1) or (2), wherein $Z^1$, $Z^2$ and $Z^3$ in the general formula (1) each independently represent a substituted amino group, a substituted or unsubstituted aryl group or a substituted or unsubstituted heteroaryl group.

(4) The light-emitting material according to the item (1) or (2), wherein $Z^1$, $Z^2$ and $Z^3$ in the general formula (1) each independently represent a substituted or unsubstituted diarylamino group.

(5) The light-emitting material according to the item (4), wherein the compound has a structure represented by the following general formula (2):

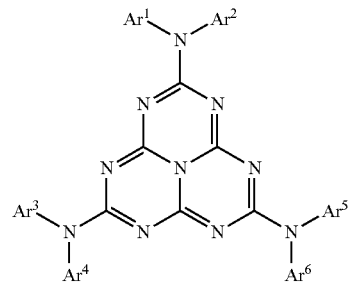

General Formula (2)

wherein in the general formula (2), $Ar^1$, $Ar^2$, $Ar^3$, $Ar^4$, $Ar^5$ and $Ar^6$ each independently represent a substituted or unsubstituted aryl group.

(6) The light-emitting material according to the item (1) or (2), wherein $Z^1$, $Z^2$ and $Z^3$ in the general formula (1) each independently represent an aryl group substituted by a substituted or unsubstituted diarylamino group.

(7) The light-emitting material according to the item (6), wherein the compound has a structure represented by the following general formula (3):

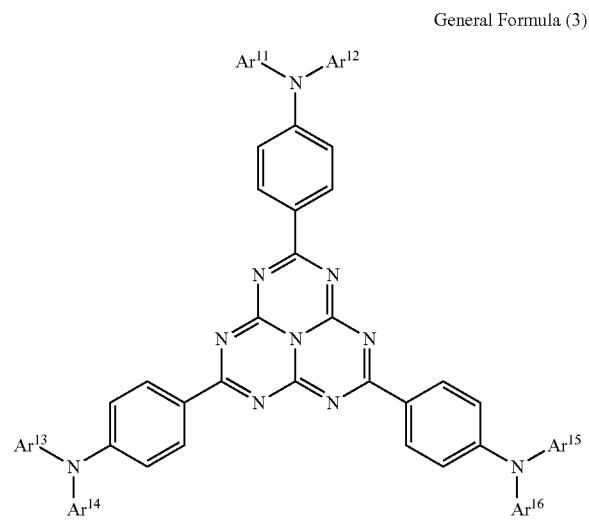

General Formula (3)

wherein in the general formula (3), $Ar^{11}$, $Ar^{12}$, $Ar^{13}$, $Ar^{14}$, $Ar^{15}$ and $Ar^{16}$ each independently represent a substituted or unsubstituted aryl group.

(8) A delayed fluorescence emitter having a structure represented by the general formula (1).

(9) An organic light-emitting device containing the light-emitting material according to any one of the items (1) to (8) as a light-emitting material.

(10) The organic light-emitting device according to the item (9), which is an organic electroluminescent device containing an anode, a cathode, and at least one organic layer containing a light-emitting layer between the anode and the cathode, and contains the light-emitting material in the light-emitting layer.

(11) The organic light-emitting device according to the item (9) or (10), which emits delayed fluorescent light.

Advantageous Effects of Invention

The compound represented by the general formula (1) is useful as a light-emitting material of an organic light-emitting device. The group of the compounds represented by the general formula (1) includes one that exhibits emission of delayed fluorescent light and one that has an extremely high light emission efficiency. The organic light-emitting device of the invention includes one that exhibits emission of delayed fluorescent light and one that has an extremely high light emission efficiency.

DESCRIPTION OF EMBODIMENTS

Figure 1:
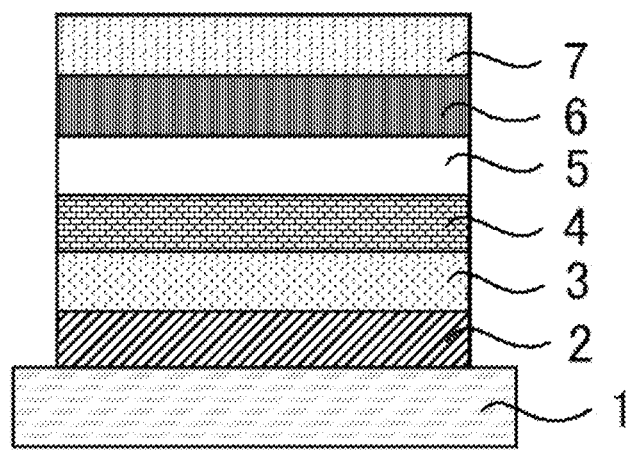
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the present specification, a numerical range expressed by "from X to Y" means a range including the numerals X and Y as the lower limit and the upper limit, respectively.

Compound Represented by General Formula (1)

The compound of the invention has a structure represented by the following general formula (1).

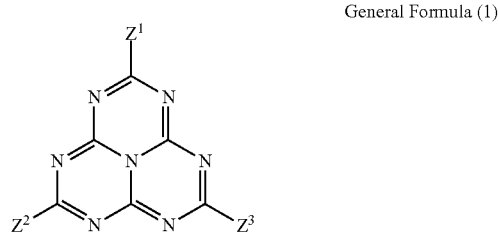

General Formula (1)

In the general formula (1), $Z^1$, $Z^2$ and $Z^3$ each independently represent a substituent. The substituent referred to herein means atoms or atomic groups other than a hydrogen atom.

Preferred examples of the substituent represented by $Z^1$, $Z^2$ and $Z^3$ include a substituted amino group, a substituted or unsubstituted aryl group and a substituted or unsubstituted heteroaryl group. $Z^1$, $Z^2$ and $Z^3$ may be the same as or different from each other. What is preferred is the case where $Z^1$, $Z^2$ and $Z^3$ are the same as each other.

The substituted amino group that may be represented by $Z^1$, $Z^2$ and $Z^3$ is a group having a structure represented by —N(R¹)(R²), wherein R¹ and R² each independently represent a substituent. R¹ and R² each are preferably a substituted or unsubstituted alkyl group, a substituted or unsubstituted aryl group or a substituted or unsubstituted heteroaryl group, more preferably a substituted or unsubstituted aryl group or a substituted or unsubstituted heteroaryl group, and further preferably a substituted or unsubstituted aryl group. R¹ and R² may be the same as or different from each other, and are preferably the same as each other. R¹ and R² may be bonded to each other to form a cyclic structure. Specific examples of the group forming the cyclic structure include a carbazolyl group. Particularly preferred examples of the substituted amino group that may be represented by $Z^1$, $Z^2$ and $Z^3$ include a substituted or unsubstituted diarylamino group, and specific examples thereof include a diphenylamino group and a di(4-fluorophenyl) amino group.

The aryl group that may be represented by $Z^1$, $Z^2$ and $Z^3$ may be formed of only one aromatic ring or may have a structure containing two or more aromatic rings that are fused to each other. The aryl group preferably has from 6 to 22 carbon atoms, more preferably from 6 to 18 carbon atoms, further preferably from 6 to 14 carbon atoms, and still further preferably from 6 to 10 carbon atoms (i.e., a phenyl group, a 1-naphthyl group or a 2-naphthyl group). The aryl group may be substituted, and the substituent in this case is preferably a halogen atom, a substituted amino group, a substituted or unsubstituted alkyl group, a substituted or unsubstituted aryl group or a substituted or unsubstituted heteroaryl group, and more preferably a halogen atom or a substituted amino group. In the case where the aryl group that may be represented by $Z^1$, $Z^2$ and $Z^3$ is substituted, the number of the substituent is preferably from 1 to 5, more preferably from 1 to 4, and further preferably from 1 to 3. In the case where the aryl group has plural substituents, the substituents may be the same as or different from each other. Particularly preferred examples of the substituted or unsubstituted aryl group that may be represented by $Z^1$, $Z^2$ and $Z^3$ include an aryl group that is substituted by a diarylamino group. Specific examples thereof include a 4-(diphenylamino)phenyl group, a 4-(di(4-tert-butylphenyl)amino) phenyl group, a 4-(di(4-methylphenyl)amino)phenyl group, a 4-(di(4-ethylphenyl)amino)phenyl group, a 4-(di(4-propylphenyl)amino)phenyl group, 4-(di(4-isopropylphenyl) amino)phenyl group, a 4-(di(3,5-dimethylphenyl)amino) phenyl group, a 4-(di(3,5-diethylphenyl)amino)phenyl group, a 4-(di(2,4,6-trimethylphenyl)amino)phenyl group, a 4-(di(1-naphthyl)amino)phenyl group and a 4-(di(2-naphthyl) amino)phenyl group.

The heteroaryl group that may be represented by $Z^1$, $Z^2$ and $Z^3$ may be formed of only one ring or may have a structure containing two or more rings that are fused to each other. The heteroaryl group preferably has from 3 to 21 carbon atoms, more preferably from 3 to 17 carbon atoms, further preferably from 3 to 13 carbon atoms, and still further preferably from 3 to 9 carbon atoms. The heteroaryl group may be substituted, and the substituent in this case is preferably a halogen atom, a substituted amino group, a substituted or unsubstituted alkyl group, a substituted or unsubstituted aryl group or a substituted or unsubstituted heteroaryl group, and more preferably a halogen atom or a substituted amino group. In the case where the heteroaryl group that may be represented by $Z^1$, $Z^2$ and $Z^3$ is substituted, the number of the substituent is preferably from 1 to 4, more preferably from 1 to 3, and further preferably from 1 or 2. In the case where the heteroaryl group has plural substituents, the substituents may be the same as or different from each other.

The alkyl group referred to herein may be either linear, branched or cyclic. What is preferred is a linear or branched alkyl group. The alkyl group preferably has from 1 to 20 carbon atoms, more preferably from 1 to 12 carbon atoms, further preferably from 1 to 6 carbon atoms, and still further preferably from 1 to 3 carbon atoms (i.e., a methyl group, an ethyl group, a n-propyl group or an isopropyl group). Examples of the cyclic alkyl group include a cyclopentyl group, a cyclohexyl group and a cycloheptyl group.

The halogen atom referred to herein is preferably a fluorine atom, a chlorine atom, a bromine atom or an iodine atom, more preferably a fluorine atom, a chlorine atom or a bromine atom, and further preferably a fluorine atom or a chlorine atom.

Examples of the substituent on the alkyl group, the aryl group and the heteroaryl group include a substituted or unsubstituted alkyl group, a substituted or unsubstituted aryl group, a substituted or unsubstituted heteroaryl group, a substituted or unsubstituted alkoxy group, a substituted or unsubstituted aryloxy group and a substituted or unsubstituted heteroaryloxy group. The preferred ranges of the alkyl group, the aryl group and the heteroaryl group that may be used as the substituent are the same as described above. The alkoxy group that may be used as the substituent may be either linear, branched or cyclic. What is preferred is a linear or branched alkoxy group. The alkoxy group preferably has from 1 to 20 carbon atoms, more preferably from 1 to 12 carbon atoms, further preferably from 1 to 6 carbon atoms, still further preferably from 1 to 3 carbon atoms (i.e., a methoxy group, an ethoxy group, a n-propoxy group or an isopropoxy group). Examples of the cyclic alkoxy group include a cyclopenthyloxy group, a cyclohexyloxy group and a cycloheptyloxy group. The aryloxy group that may be used as the substituent may be formed of only one aromatic ring or may have a structure containing two or more aromatic rings that are fused to each other. The aryloxy group preferably has from 6 to 22 carbon atoms, more preferably from 6 to 18 carbon atoms, further preferably from 6 to 14 carbon atoms, and still further preferably from 6 to 10 carbon atoms (i.e., a phenyloxy group, a 1-naphthyloxy group or a 2-naphthyloxy group). The heteroaryloxy group that may be used as the substituent may be formed of only one ring or may have a structure containing two or more rings that are fused to each other. The heteroaryloxy group preferably has from 3 to 21 carbon atoms, more preferably from 3 to 17 carbon atoms, further preferably from 3 to 13 carbon atoms, and still further preferably from 3 to 9 carbon atoms.

The compound of the invention preferably has a structure represented by the following general formula (2).

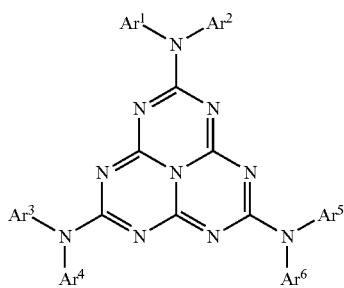

General Formula (2)

In the general formula (2), $Ar^1$, $Ar^2$, $Ar^3$, $Ar^4$, $Ar^5$ and $Ar^6$ each independently represent a substituted or unsubstituted aryl group. $Ar^1$, $Ar^2$, $Ar^3$, $Ar^4$, $Ar^5$ and $Ar^6$ may be the same as or different from each other, and what is preferred is the case where all $Ar^1$, $Ar^2$, $Ar^3$, $Ar^4$, $Ar^5$ and $Ar^6$ are the same as each other. $Ar^1$ and $Ar^2$ may be bonded to form a cyclic structure with the N atom. $Ar^3$ and $Ar^4$ may be bonded to form a cyclic structure with the N atom. $Ar^5$ and $Ar^6$ may be bonded to form a cyclic structure with the N atom. For descriptions and specific examples for the substituted or unsubstituted aryl group that may be represented by $Ar^1$, $Ar^2$, $Ar^3$, $Ar^4$, $Ar^5$ and $Ar^6$, reference may be made to the descriptions and the specific examples of the substituted or unsubstituted aryl group in the description for the general formula (1).

Specific examples of the compound represented by the general formula (2) include a compound represented by the following structural formula.

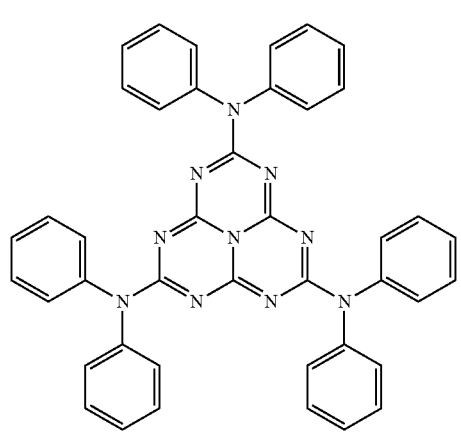

Compound 1

Specific examples of the compound represented by the general formula (2) include compounds described in the following table. In the table, all $Ar^1$, $Ar^2$, $Ar^3$, $Ar^4$, $Ar^5$ and $Ar^6$ are the same as each other, and are collectively referred to as Ar.

TABLE 1

| Compound No. | Ar |
|---|---|
| 2 | 4-fluorophenyl |
| 3 | 3-fluorophenyl |
| 4 | 2-fluorophenyl |
| 5 | 3,5-difluorophenyl |
| 6 | 2,4,6-trifluorophenyl |

TABLE 1-continued

| Compound No. | Ar |
|---|---|
| 7 | 4-methylphenyl |
| 8 | 3-methylphenyl |
| 9 | 2-methylphenyl |
| 10 | 3,5-dimethylphenyl |
| 11 | 2,4,6-trimethylphenyl |
| 12 | 4-ethylphenyl |
| 13 | 3-ethylphenyl |
| 14 | 2-ethylphenyl |
| 15 | 3,5-diethylphenyl |
| 16 | 4-propylphenyl |
| 17 | 3-propylphenyl |
| 18 | 3,5-dipropylphenyl |
| 19 | 4-tert-butylphenyl |
| 20 | 3-tert-butylphenyl |
| 21 | 3,5-di-tert-butylphenyl |
| 22 | 1-naphthyl |
| 23 | 2-naphthyl |

The compound of the invention preferably has a structure represented by the following general formula (3). The group of the compounds represented by the general formula (3) is preferred particularly in the high light emission efficiency thereof.

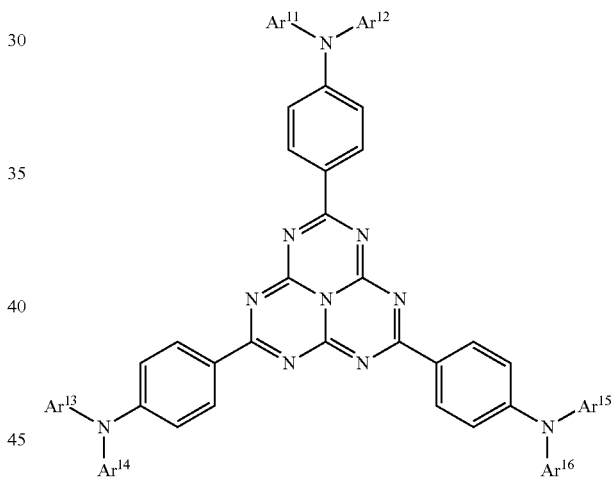

General Formula (3)

In the general formula (3), $Ar^{11}$, $Ar^{12}$, $Ar^{13}$, $Ar^{14}$, $Ar^{15}$ and $Ar^{16}$ each independently represent a substituted or unsubstituted aryl group. $Ar^{11}$, $Ar^{12}$, $Ar^{13}$, $Ar^{14}$, $Ar^{15}$ and $Ar^{16}$ may be the same as or different from each other, and what is preferred is the case where all $Ar^{11}$, $Ar^{12}$, $Ar^{13}$, $Ar^{14}$, $Ar^{15}$ and $Ar^{16}$ are the same as each other. $Ar^{11}$ and $Ar^{12}$ may be bonded to form a cyclic structure with the N atom. $Ar^{13}$ and $Ar^{14}$ may be bonded to form a cyclic structure with the N atom. $Ar^{15}$ and $Ar^{16}$ may be bonded to form a cyclic structure with the N atom. For descriptions and specific examples for the substituted or unsubstituted aryl group that may be represented by $Ar^{11}$, $Ar^{12}$, $Ar^{13}$, $Ar^{14}$, $Ar^{15}$ and $Ar^{16}$, reference may be made to the descriptions and the specific examples of the substituted or unsubstituted aryl group in the description for the general formula (1).

Specific examples of the compound represented by the general formula (3) include a compound represented by the following structural formula.

Compound 101

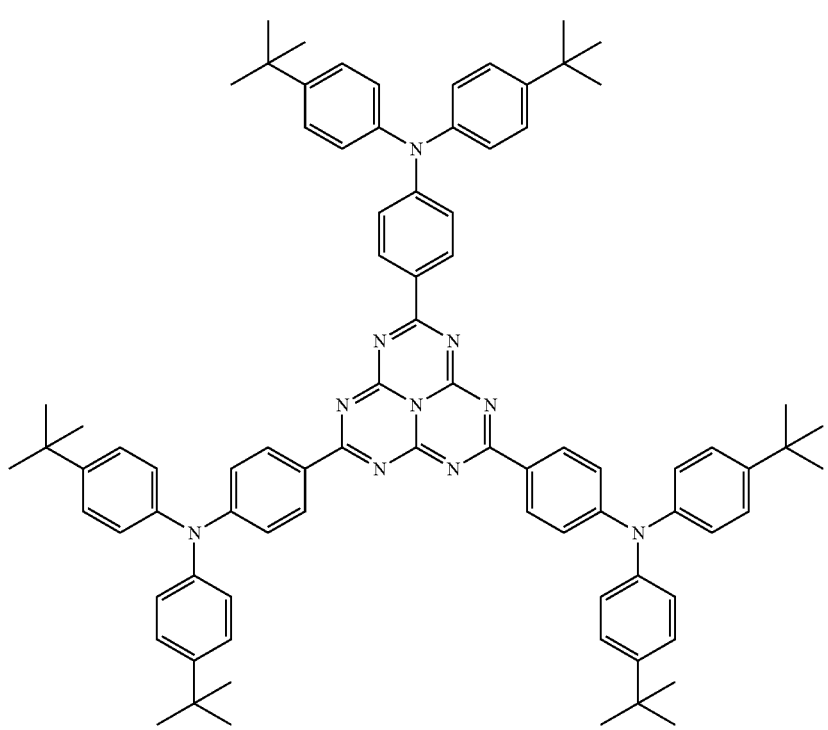

Specific examples of the compound represented by the general formula (3) include compounds described in the following table. In the table, all $Ar^{11}$, $Ar^{12}$, $Ar^{13}$, $Ar^{14}$, $Ar^{15}$ and $Ar^{16}$ are the same as each other, and are collectively referred to as Ar.

TABLE 2

| Compound No. | Ar |
|---|---|
| 102 | 4-fluorophenyl |
| 103 | 3-fluorophenyl |
| 104 | 2-fluorophenyl |
| 105 | 3,5-difluorophenyl |
| 106 | 2,4,6-trifluorophenyl |
| 107 | 4-methylphenyl |
| 108 | 3-methylphenyl |
| 109 | 2-methylphenyl |
| 110 | 3,5-dimethylphenyl |
| 111 | 2,4,6-trimethylphenyl |
| 112 | 4-ethylphenyl |
| 113 | 3-ethylphenyl |
| 114 | 2-ethylphenyl |
| 115 | 3,5-diethylphenyl |
| 116 | 4-propylphenyl |
| 117 | 3-propylphenyl |
| 118 | 3,5-dipropylphenyl |
| 119 | 4-tert-butylphenyl |
| 120 | 3-tert-butylphenyl |
| 121 | 3,5-di-tert-butylphenyl |
| 122 | 1-naphthyl |
| 123 | 2-naphthyl |

Synthesis Method of Compound Represented by General Formula (1)

The synthesis method of the compound represented by the general formula (1) is not particularly limited. The compound represented by the general formula (1) may be synthesized by combining known synthesis methods and conditions appropriately. For example, the compound may be synthesized by appropriately selecting, combining and applying the synthesis method described in the paragraphs 0039 to 0049 in JP-A-2009-501194. The compound represented by the general formula (1) may also be synthesized by combining other known synthesis reactions.

Organic Light-Emitting Device

The compound represented by the general formula (1) of the invention is useful as a light-emitting material of an organic light-emitting device. The compound represented by the general formula (1) of the invention thus may be effectively used as a light-emitting material in a light-emitting layer of an organic light-emitting device. The compound represented by the general formula (1) includes a delayed fluorescent material (delayed fluorescence emitter) emitting delayed fluorescent light. Accordingly, the invention also relates to an invention of a delayed fluorescence emitter having a structure represented by the general formula (1), an invention of the use of the compound represented by the general formula (1) as a delayed fluorescence emitter, and an invention of a method of emitting delayed fluorescent light with the compound represented by the general formula (1). An organic light-emitting device using the compound as a light-emitting material has features that the device emits delayed fluorescent light and has a high light emission efficiency. The principle of the features will be described as follows for an organic electroluminescent device as an example.

In an organic electroluminescent device, carriers injected from an anode and a cathode form an excited state for the light-emitting material, from which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum efficiency of phosphorescence may generally be often not high. A delayed fluorescent material emits fluorescent light through the mechanism that excitons excited in the triplet state, which can be formed directly in that state or indirectly processes such as intersystem crossing from a singlet state, transits to the excited triplet state after reverse intersystem crossing or the like, and then transits to the excited singlet state after reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light-emitting material of a light-emitting layer may provide an excellent organic light-emitting device, such as an organic photoluminescent device (organic PL device) and an organic electroluminescent device (organic EL device). The organic photoluminescent device has a structure containing a substrate having formed thereon at least a light-emitting layer. The organic electroluminescent device has a structure containing at least an anode, a cathode and an organic layer formed between the anode and the cathode. The organic layer contains at least a light-emitting layer, and may be formed only of a light-emitting layer, or may have one or more organic layers in addition to the light-emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescent device will be described below. The descriptions for the substrate and the light-emitting layer may also be applied to the substrate and the light-emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material, a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired shape by a photolithography method, or in the case where the pattern may not require high accuracy (for example, approximately 100 μm or more), the pattern may be formed with a mask having a desired shape on vapor deposition or sputtering of the electrode material. Alternatively, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ohm per square or less. The thickness thereof may be generally selected from a range of from 10 to 1,000 nm, and preferably from 10 to 200 nm, while depending on the material used.

Cathode

The cathode is preferably formed of as an electrode material, a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred Ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode, respectively, are recombined to form excitons, and then the layer emits light. A light-emitting material may be solely used as the light-emitting layer, but the light-emitting layer preferably contains a light-emitting material and a host material. The light-emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. There may be cases where a high light emission efficiency is obtained even though the singlet excitons and the triplet excitons may not be confined sufficiently, and therefore a host material capable of achieving a high light emission efficiency may be used in the invention without any particular limitation. In the organic light-emitting device and the organic electroluminescent device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light-emitting material contained in the light-emitting layer is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from diffusing outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from diffusing outside the light-emitting layer. Thus, the electron barrier layer and the hole barrier layer each may also have a function as an exciton barrier layer. The electron barrier layer or the exciton barrier layer referred to herein means a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through recombination of holes and electrons in the light-emitting layer from diffusing to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transporting layer, a hole barrier layer and the like may be provided. In the case where the barrier layer is provided, the material used for the barrier layer preferably has excited singlet energy and lowest excited triplet energy, at least one of which is higher than the excited singlet energy and the lowest excited triplet energy of the light-emitting material, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) may have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in the light-emitting layer but also in layers other than the light-emitting layer. In this case, the compound represented by the general formula (1) used in the light-emitting layer and the compound represented by the general formula (1) used in the layers other than the light-emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R, R' and $R_1$ to $R_{10}$ each independently represent a hydrogen atom or a substituent; X represents a carbon atom or a heteroatom that forms a cyclic structure; n represents an integer of from 3 to 5; Y represents a substituent; and m represents an integer of 0 or more.

Preferred examples of a compound that may also be used as the host material of the light-emitting layer are shown below.

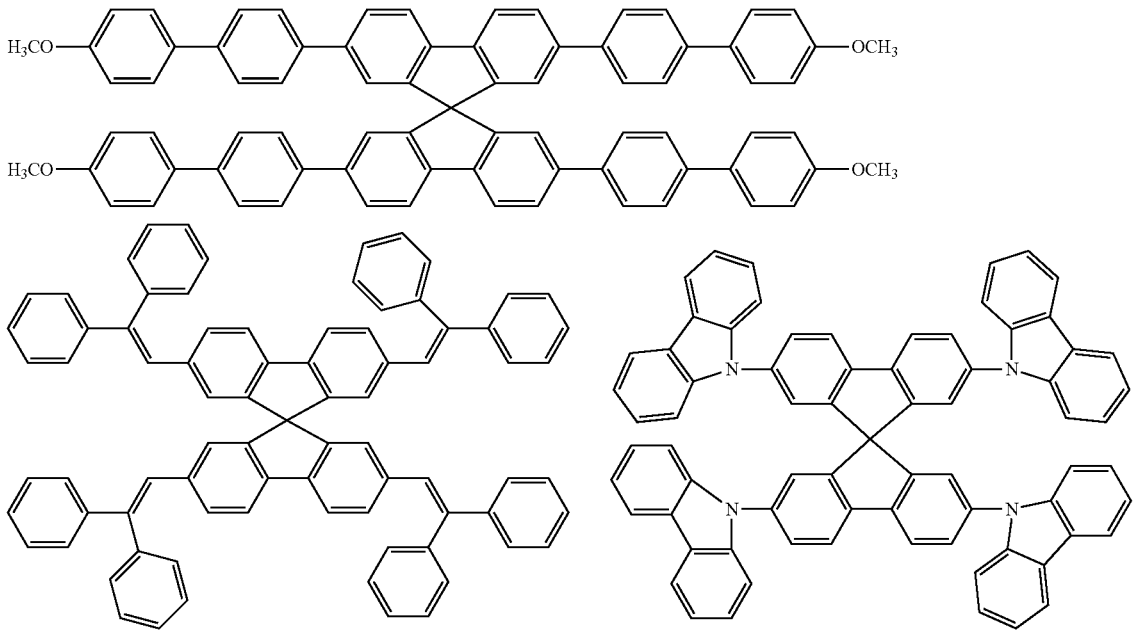

-continued
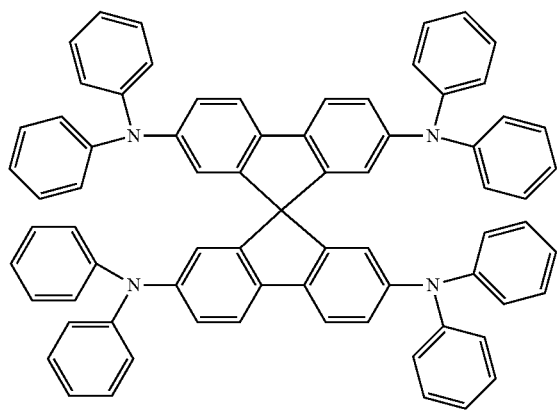
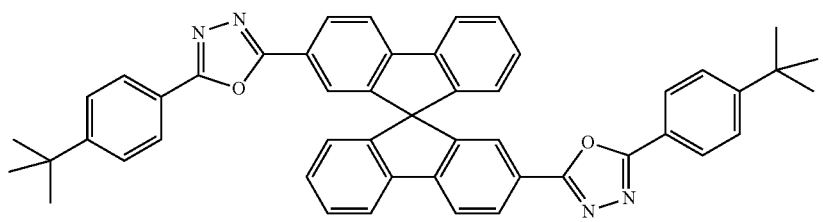
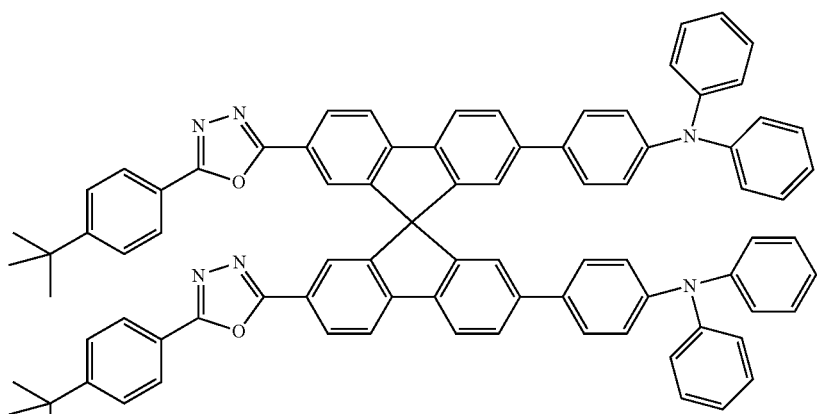
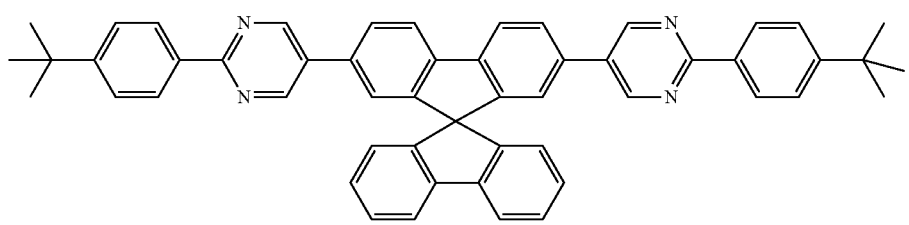
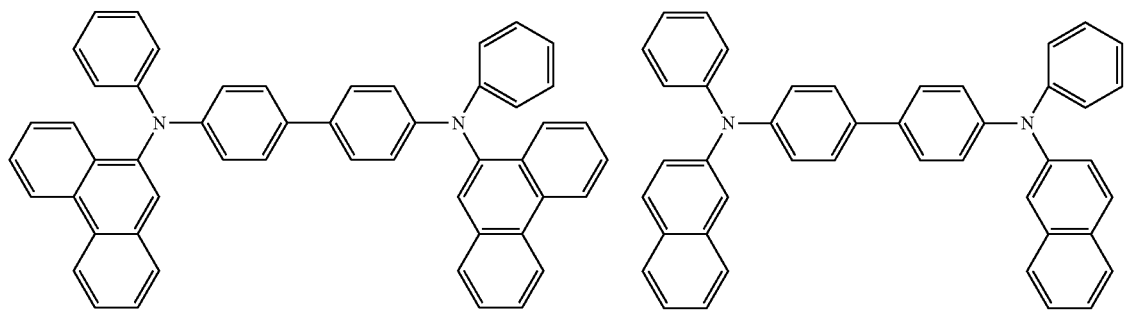

-continued
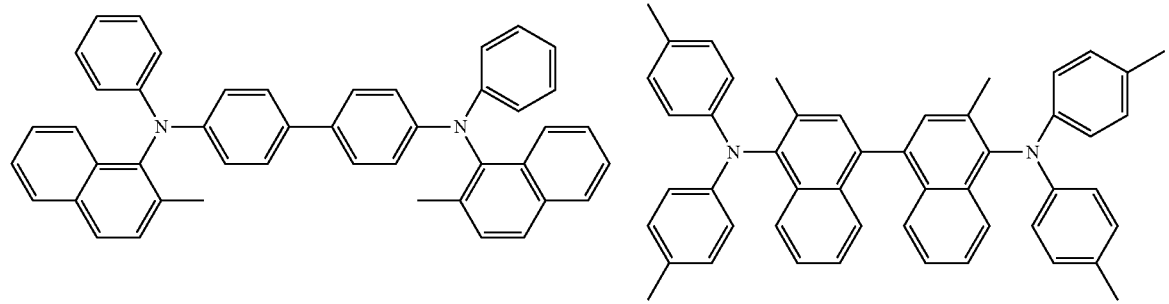
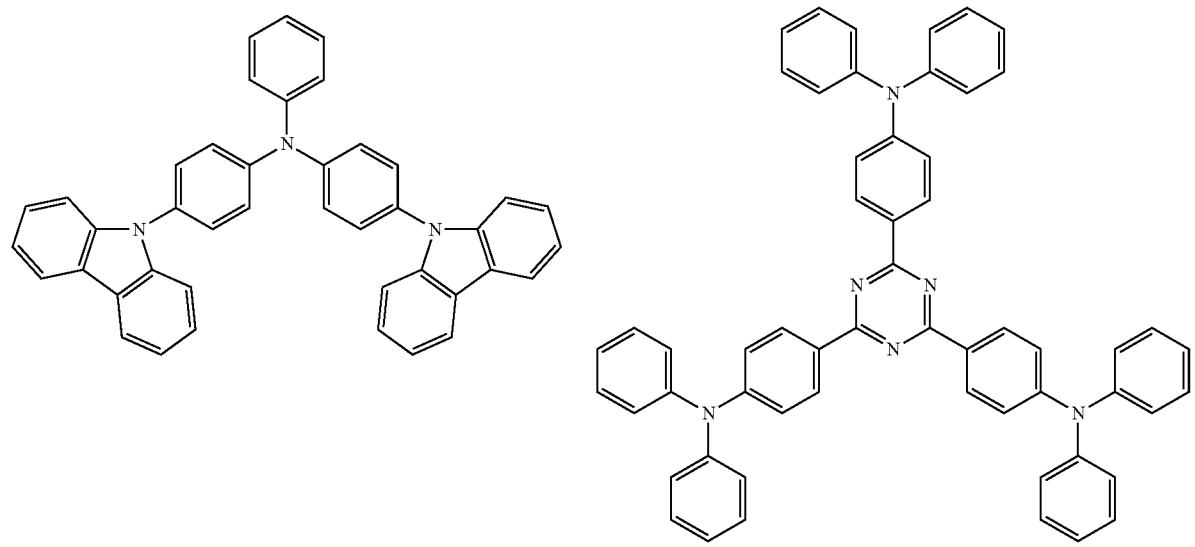
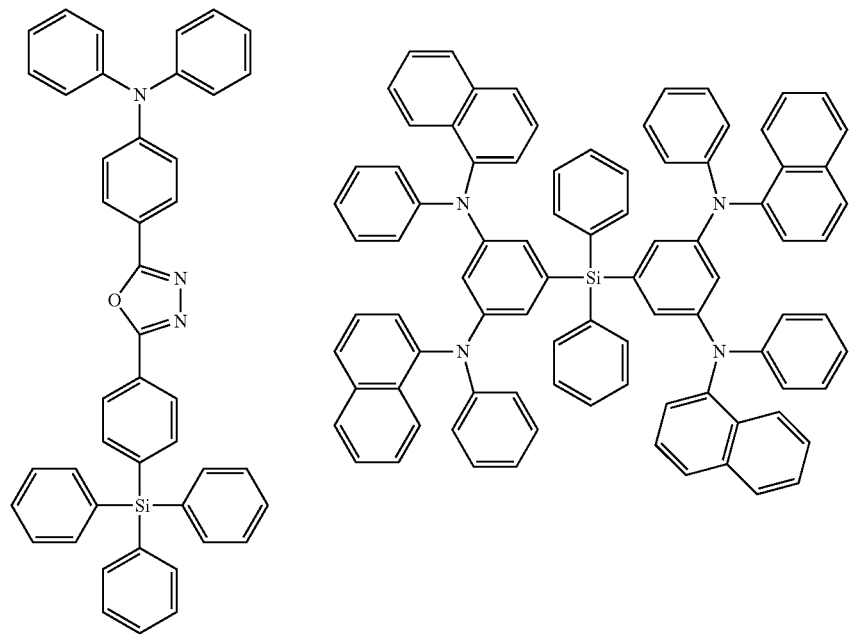

-continued
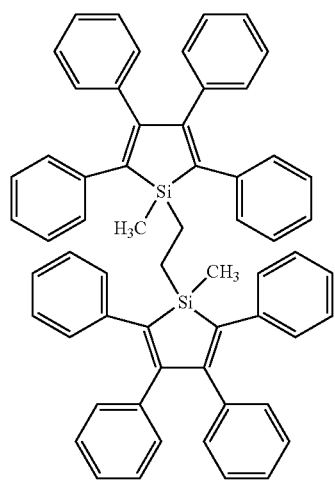 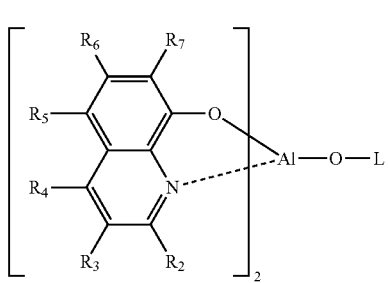
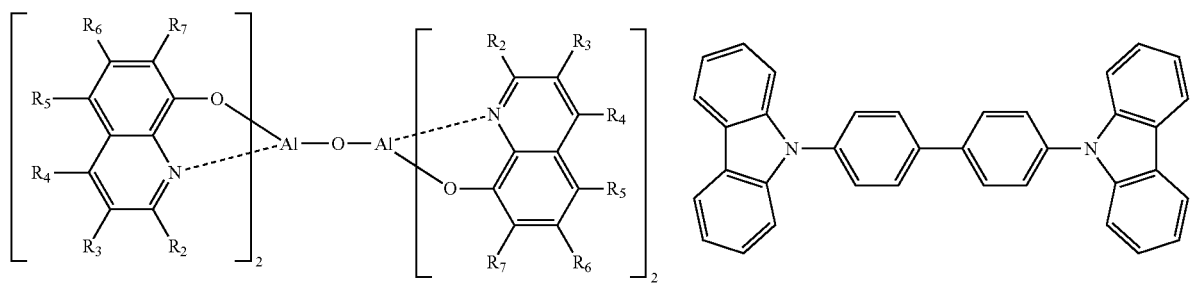
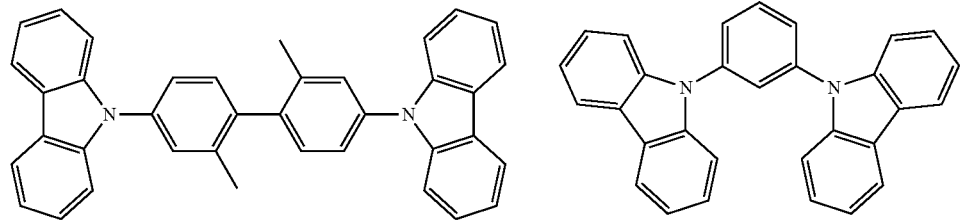
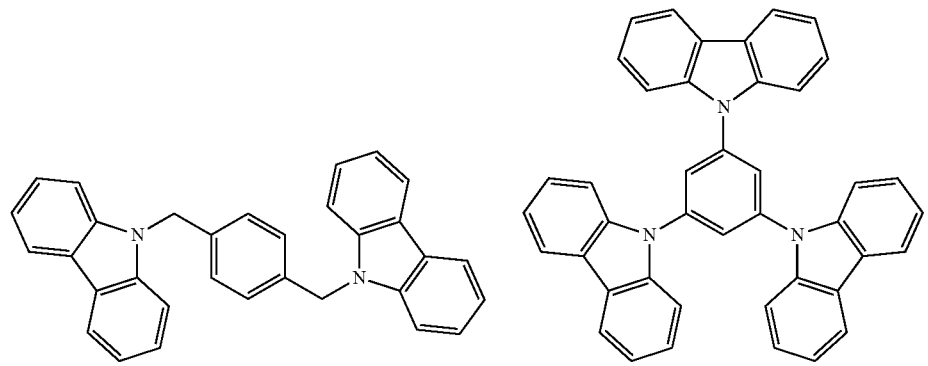
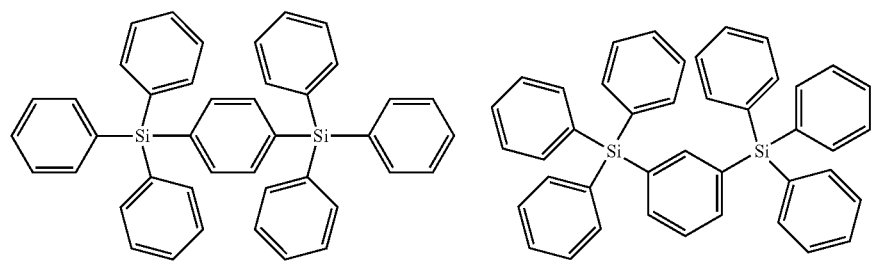

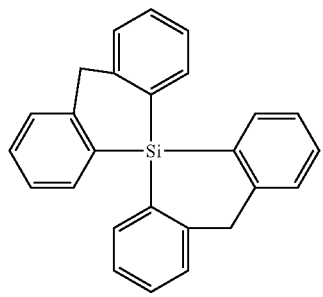
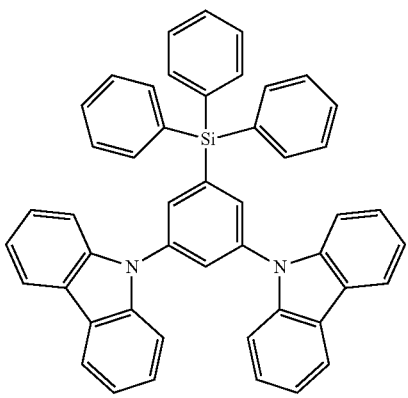
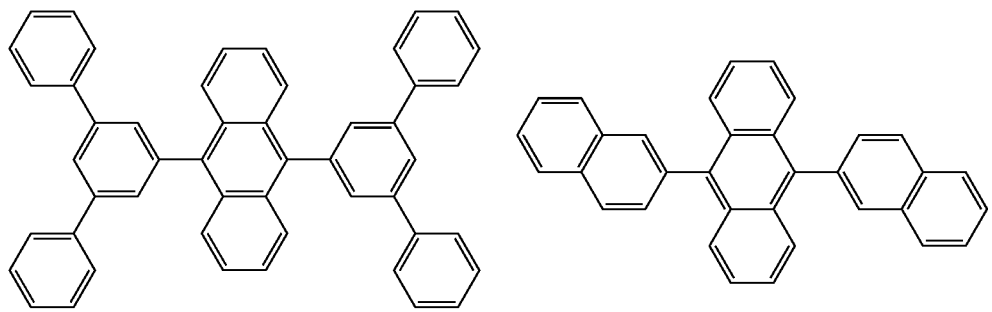
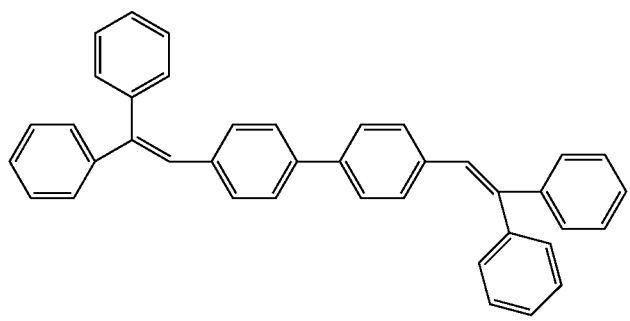
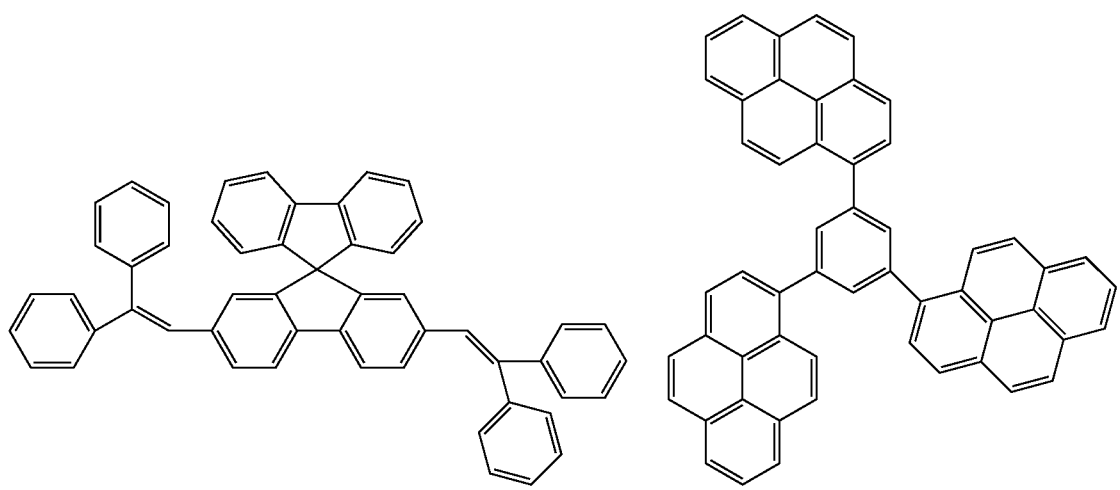

-continued
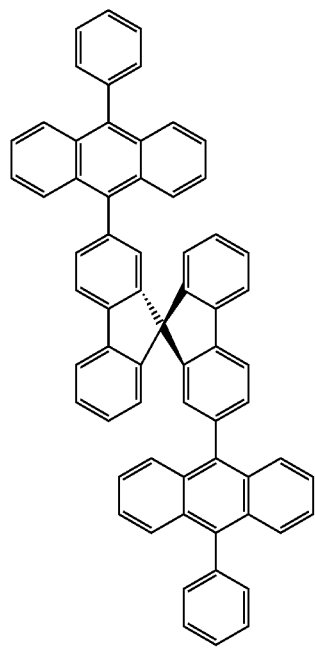
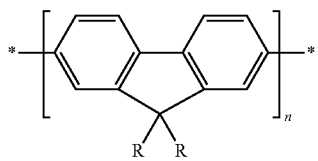
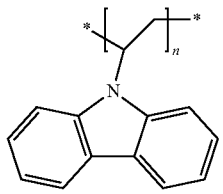
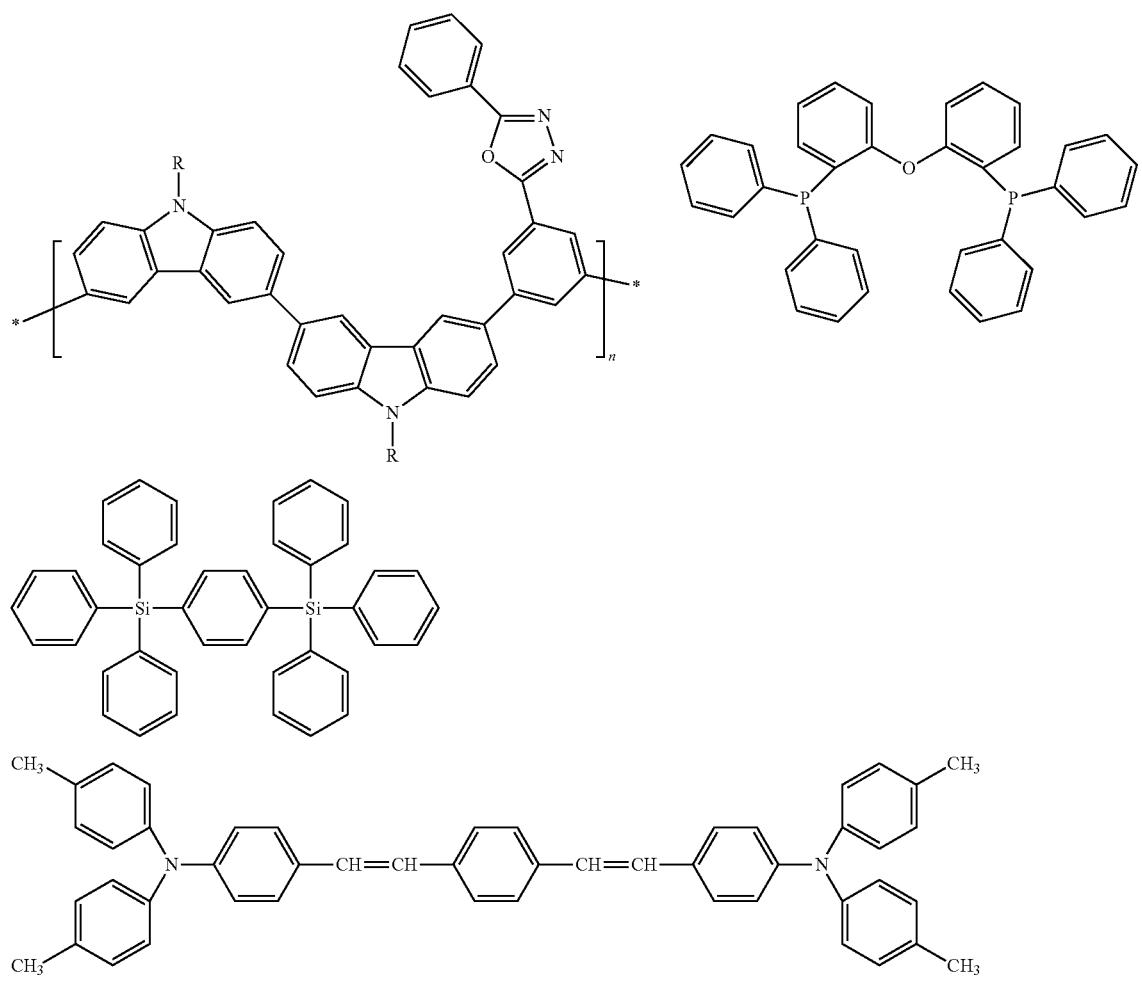

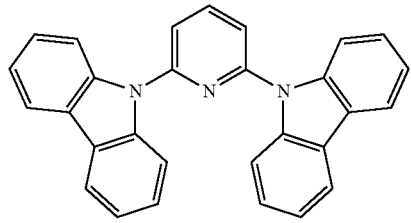
Preferred examples of a compound that may be used as the hole injection material are shown below.
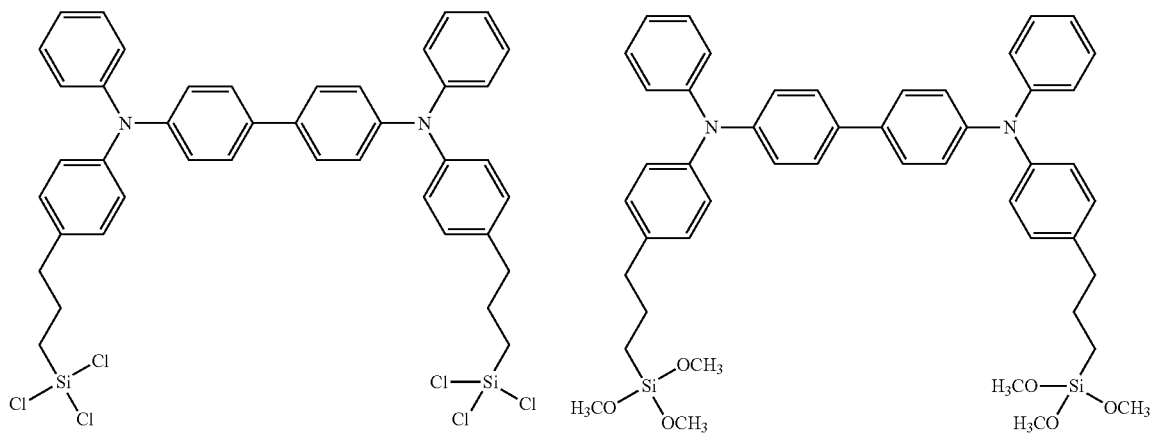
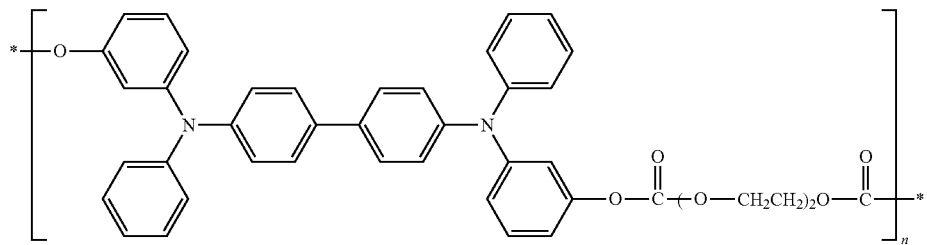
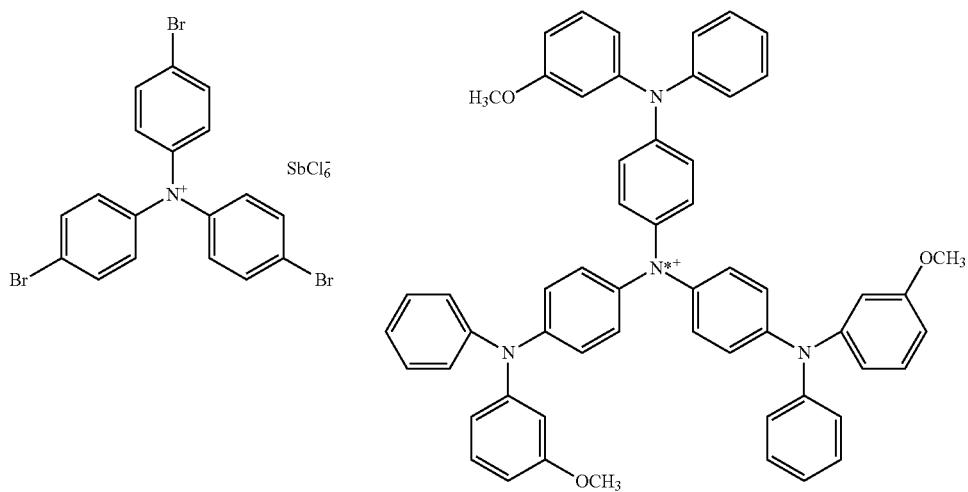

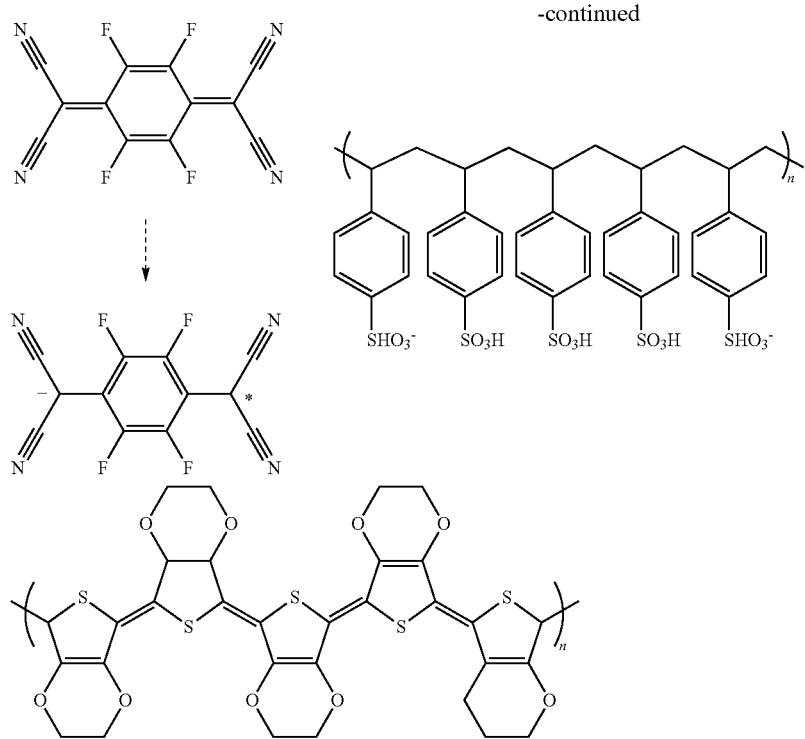
Preferred examples of a compound that may be used as the hole transporting material are shown below.
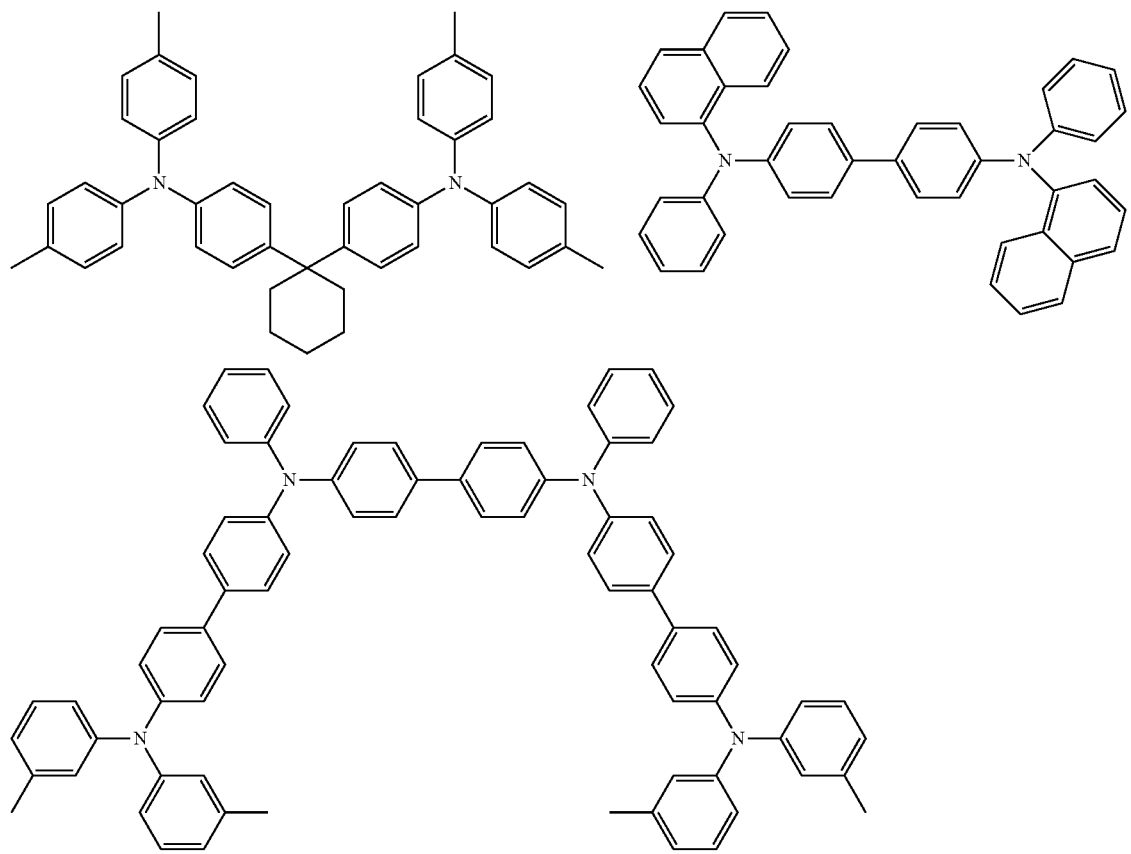

31
32
-continued
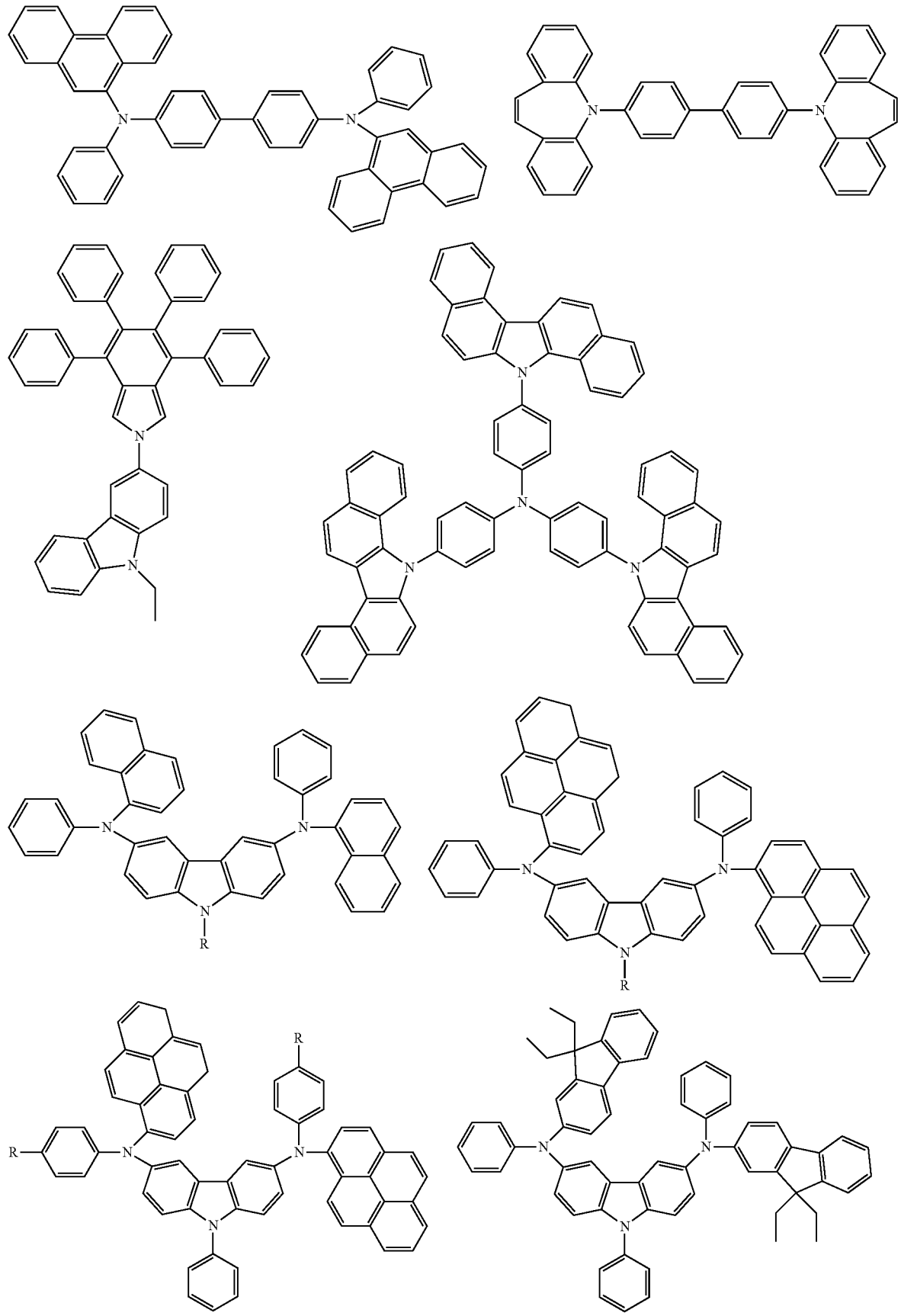

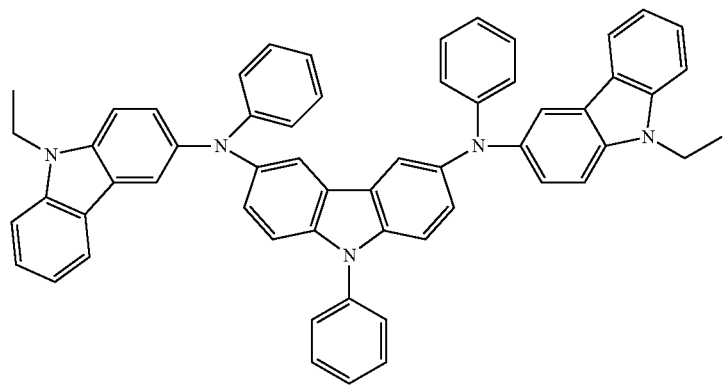
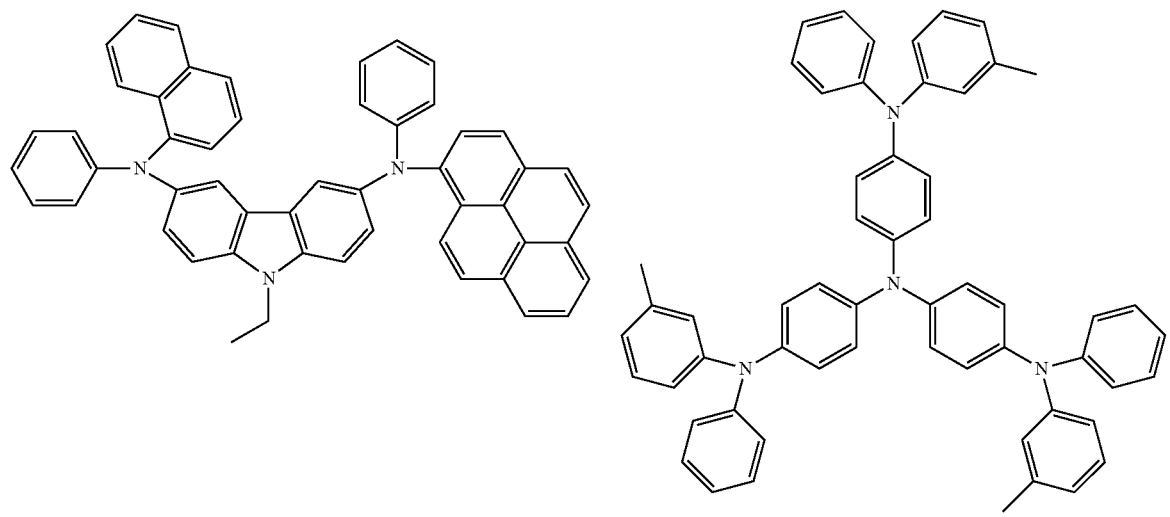
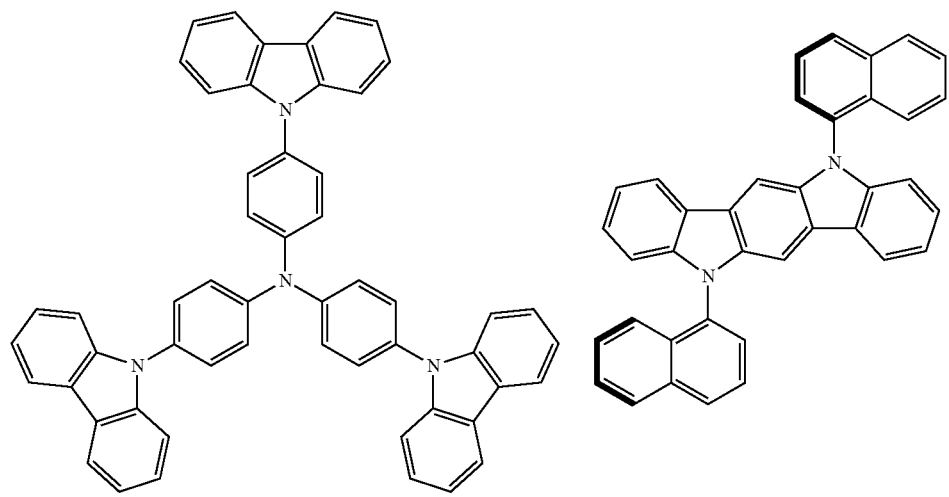

-continued
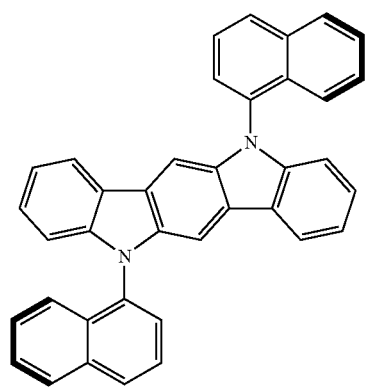
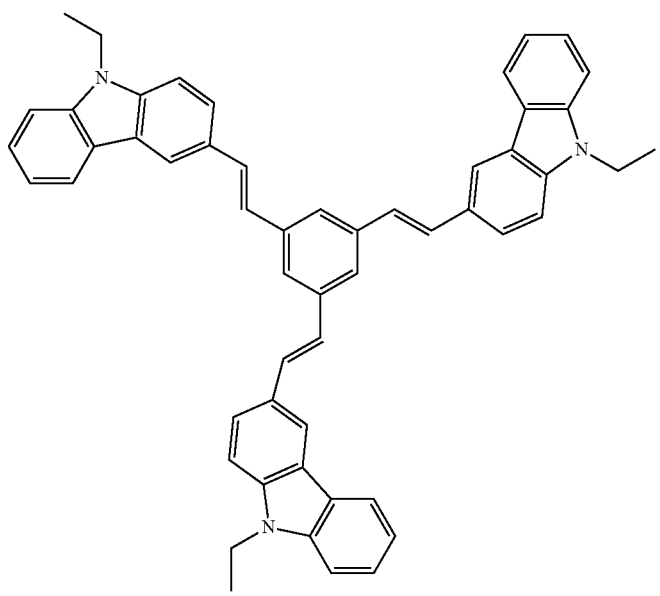
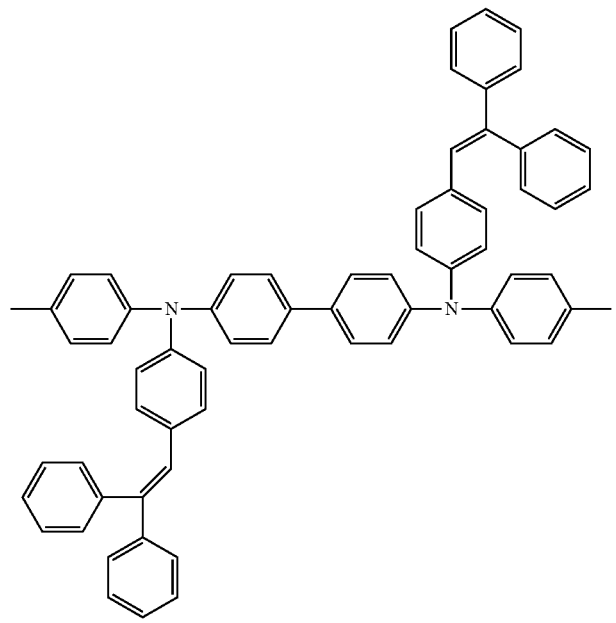
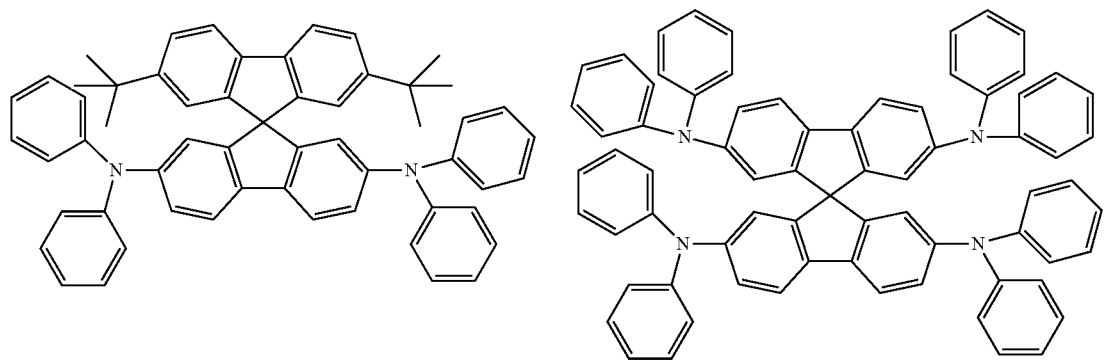

-continued
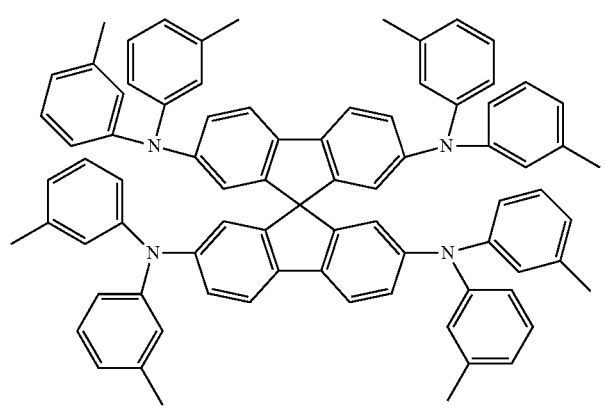
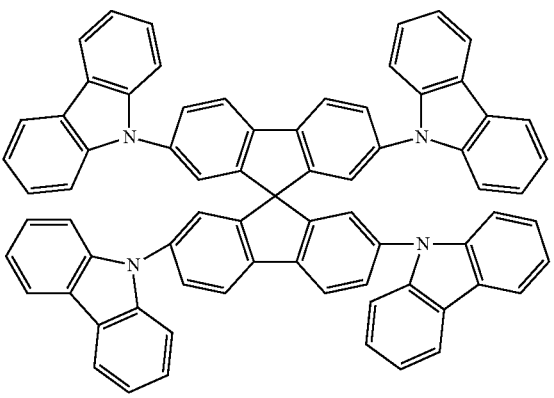
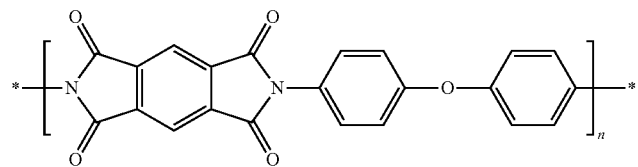
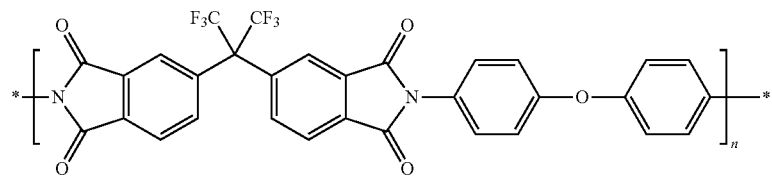
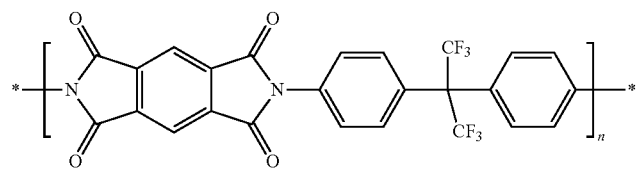
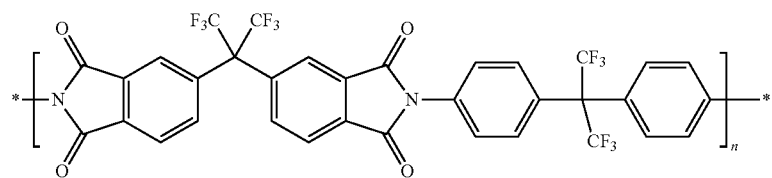

-continued
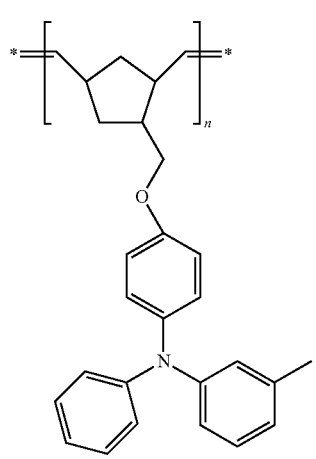
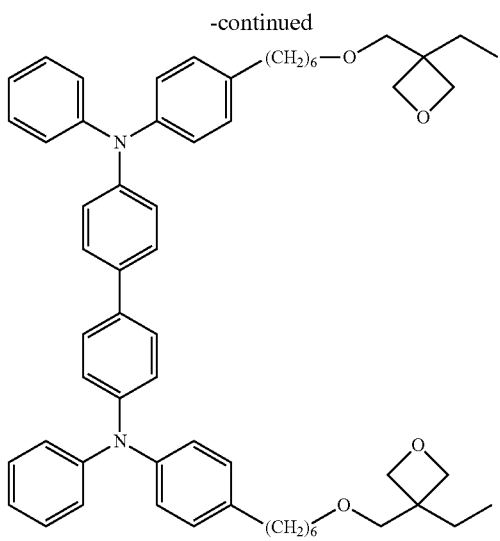
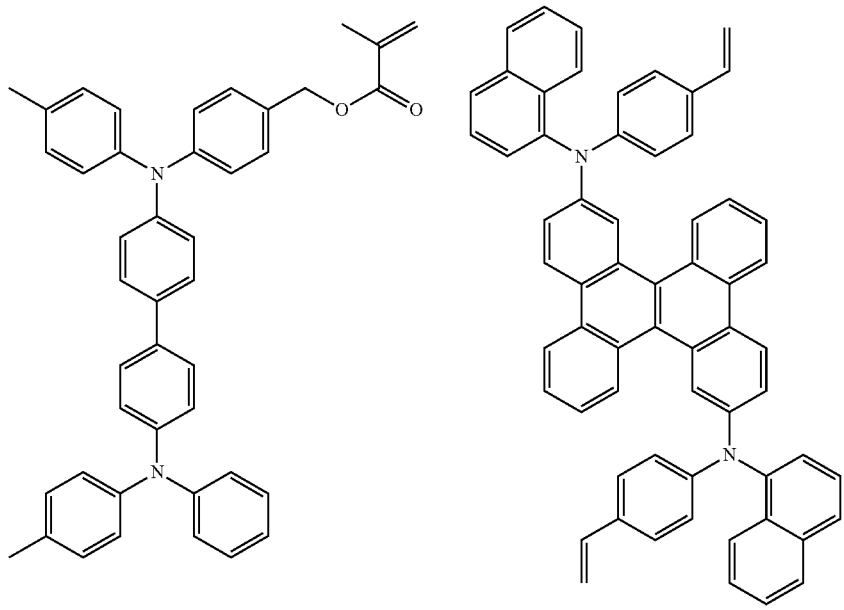
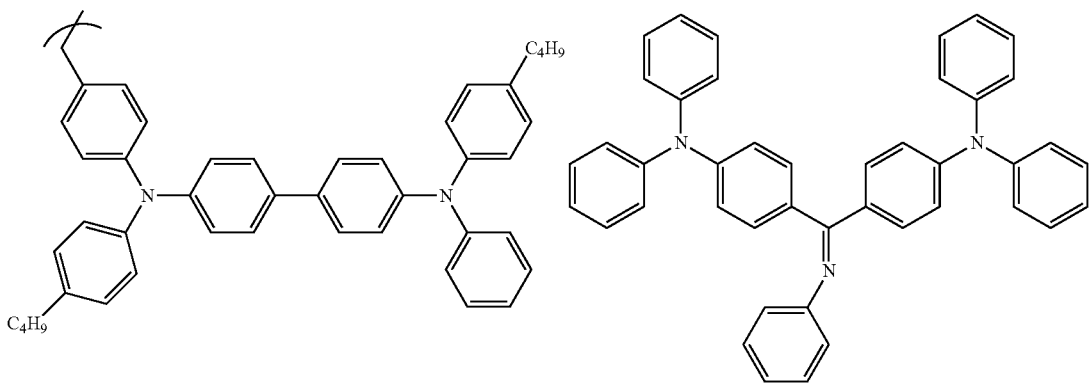

-continued
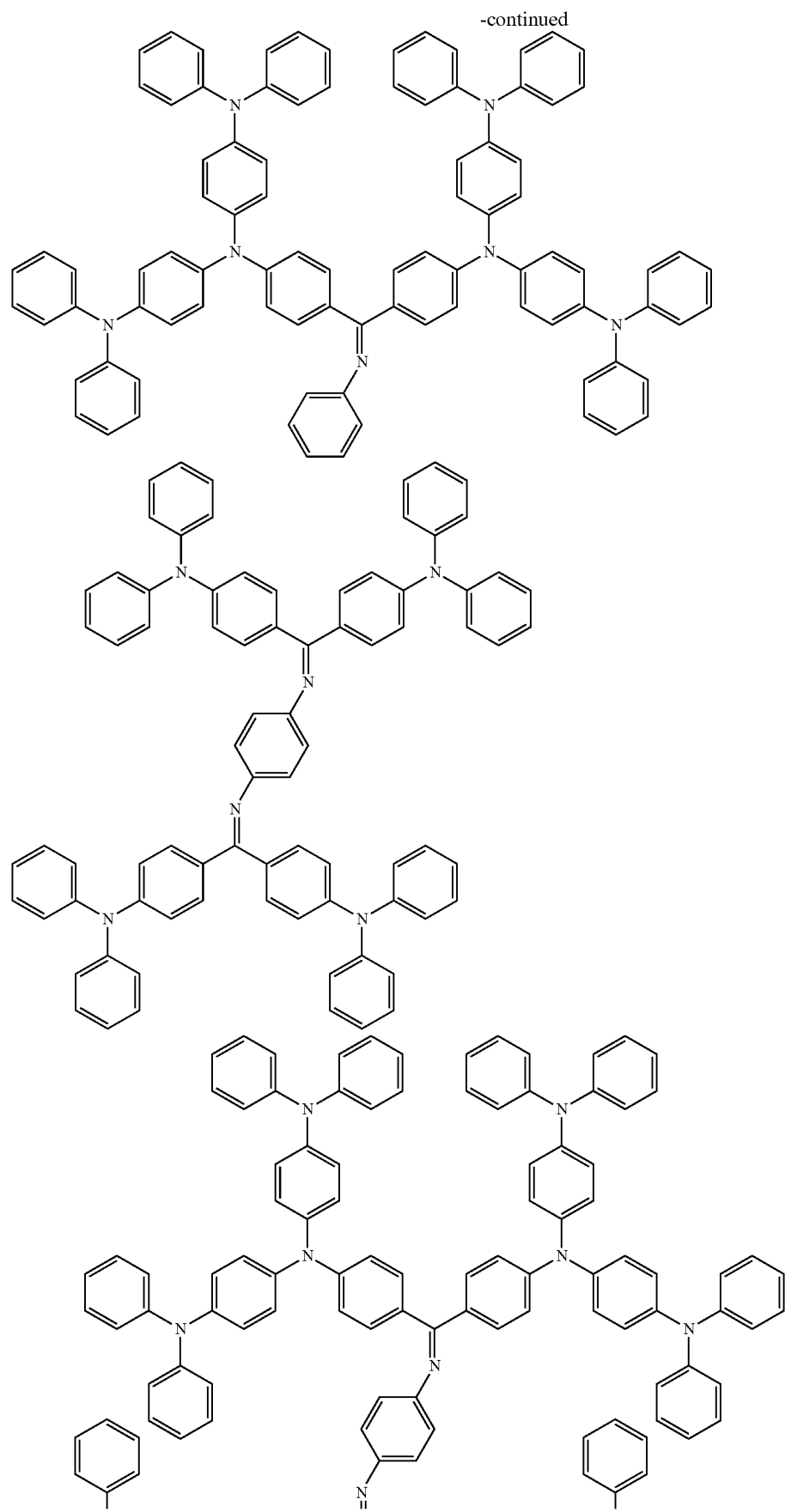

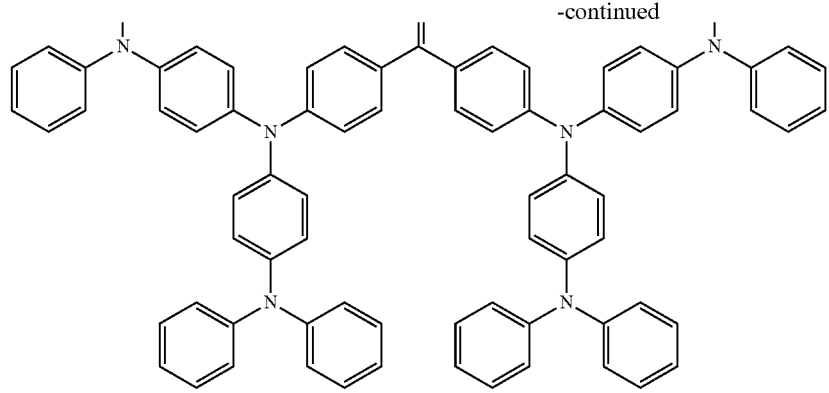
Preferred examples of a compound that may be used as the electron barrier material are shown below.
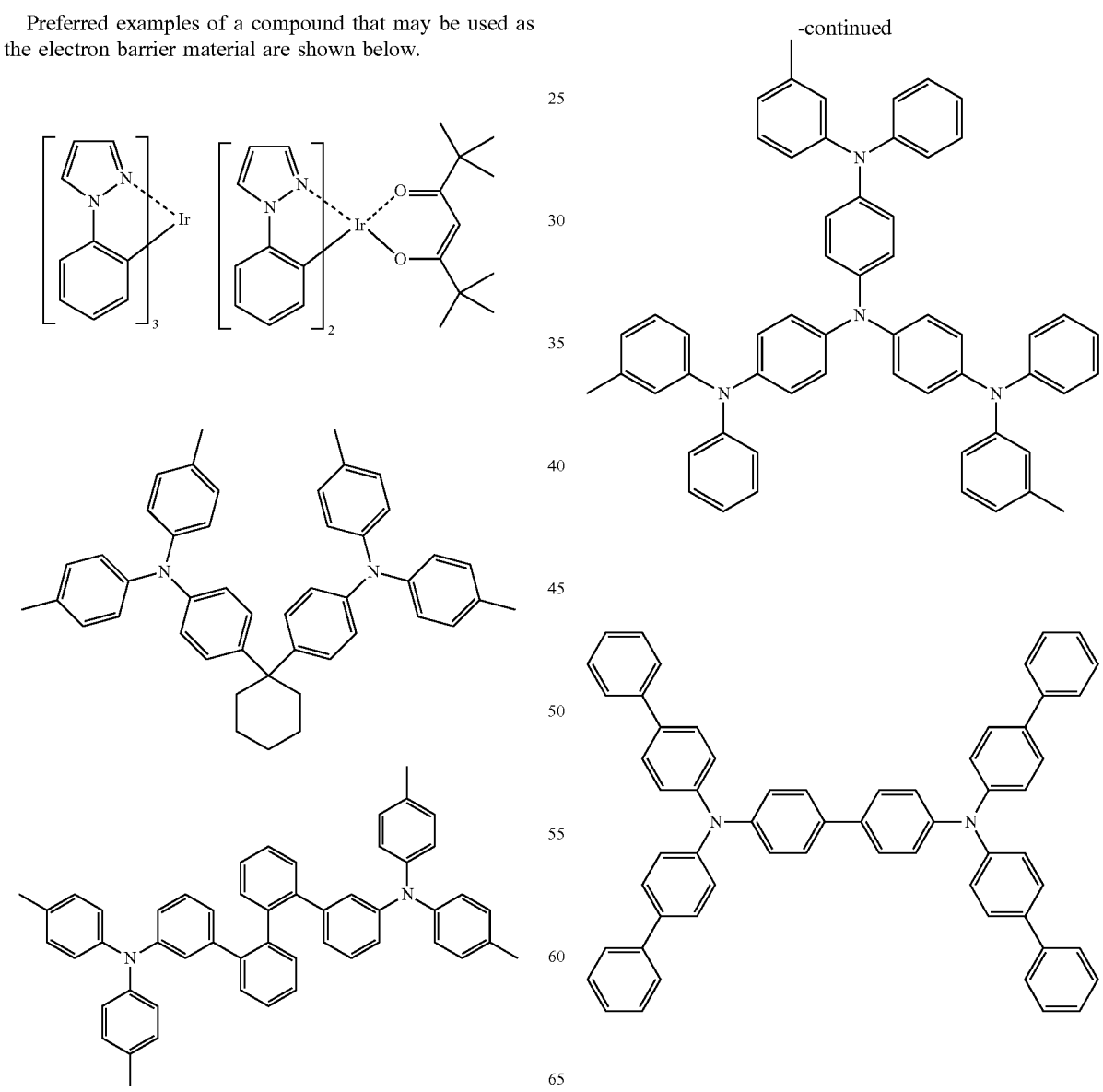
Preferred examples of a compound that may be used as the hole barrier material are shown below.

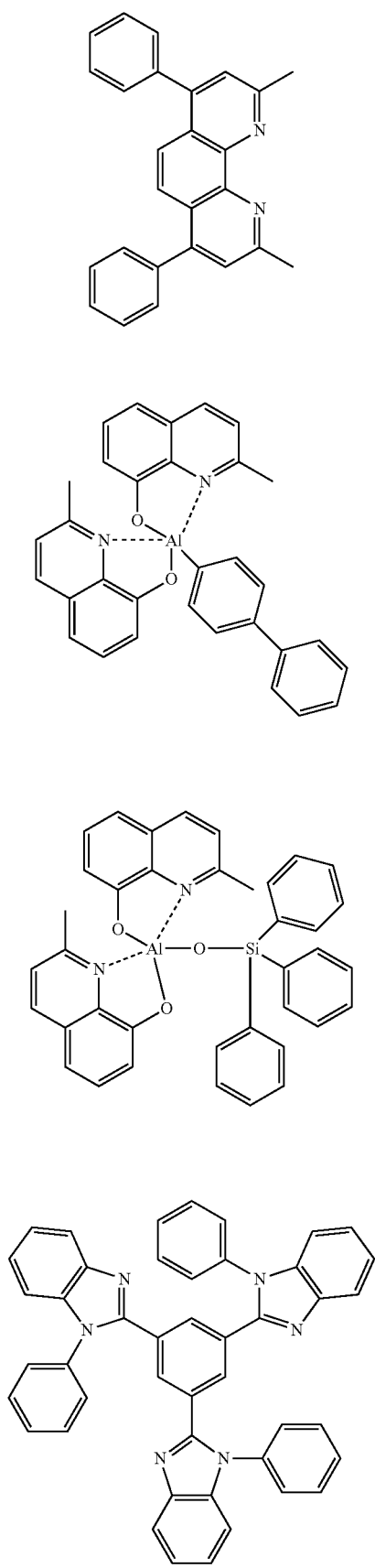
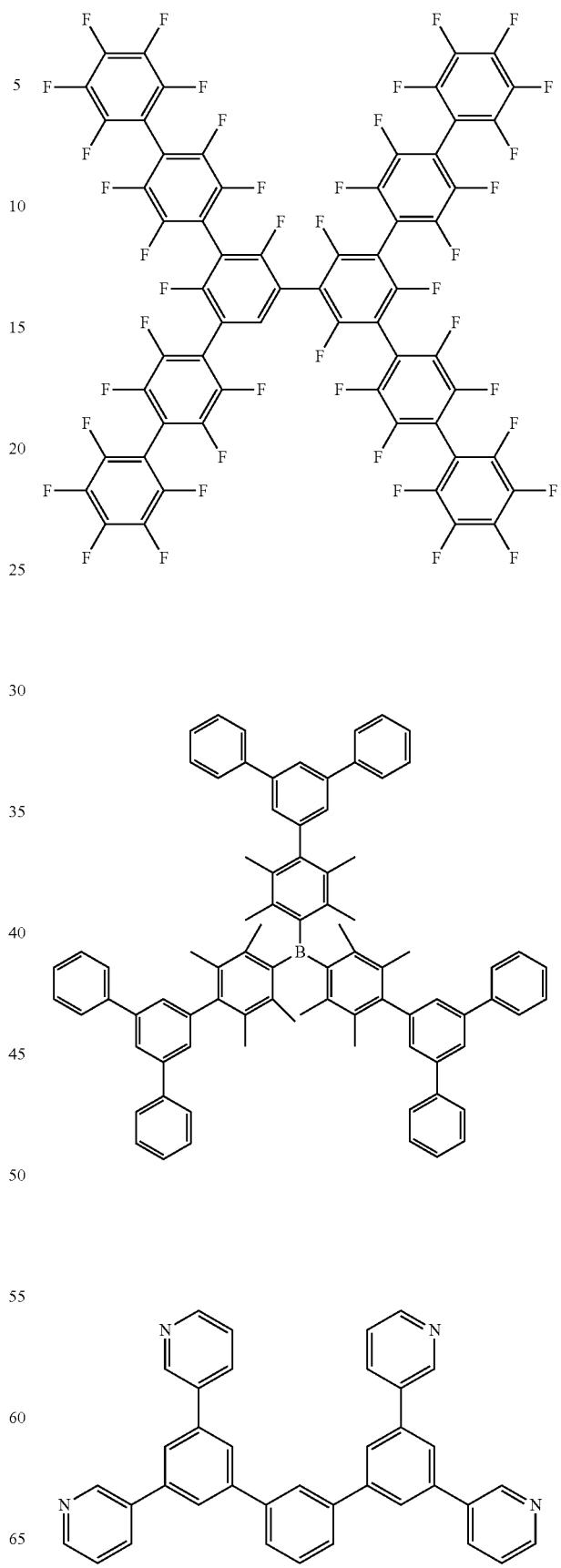

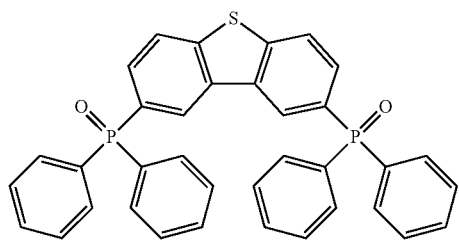
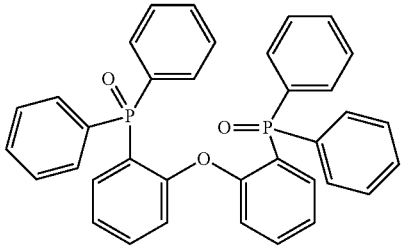 [SMILES: O=P(c1ccccc1)(c1ccccc1)c1ccccc1Oc1ccccc1P(=O)(c1ccccc1)c1ccccc1]
Preferred examples of a compound that may be used as the electron transporting material are shown below.
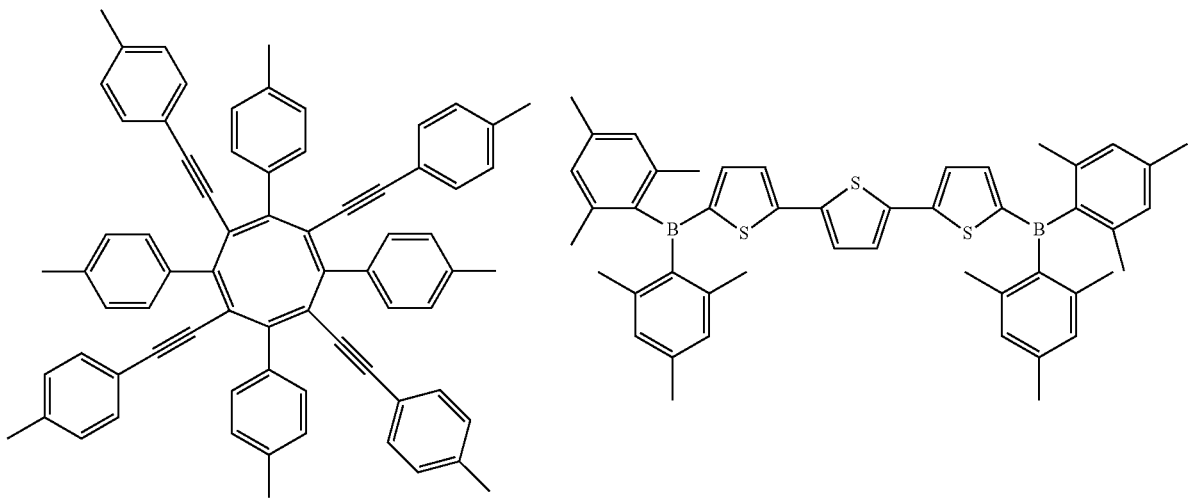
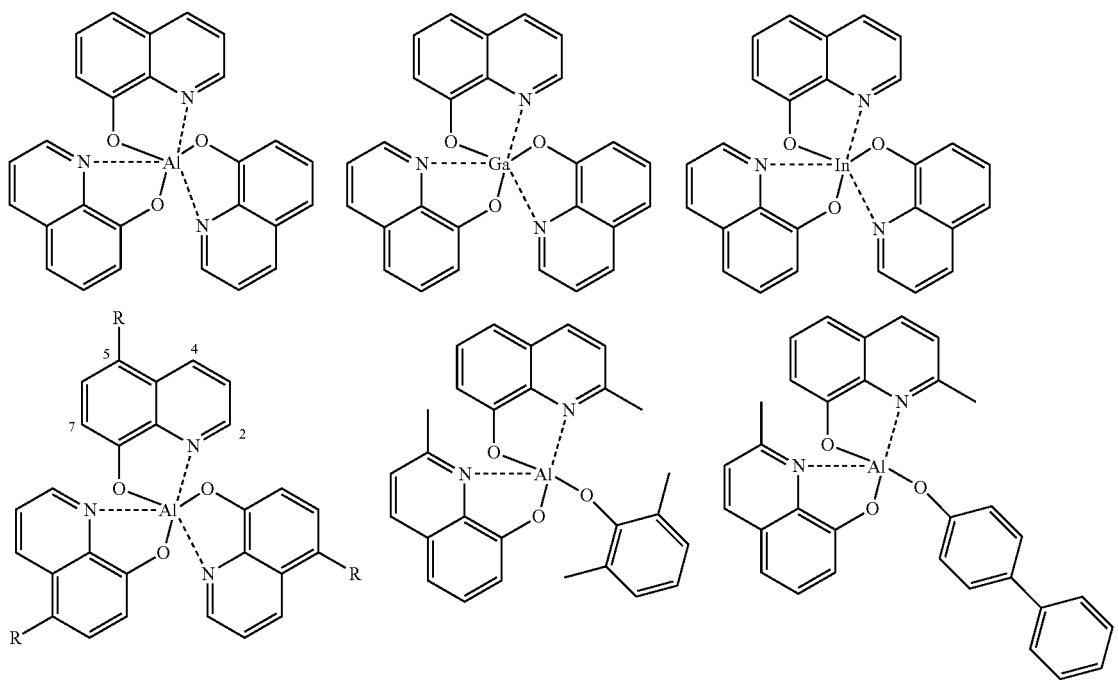

-continued
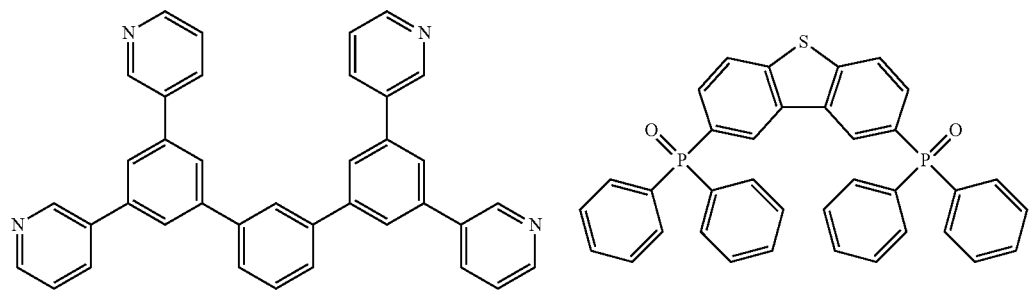
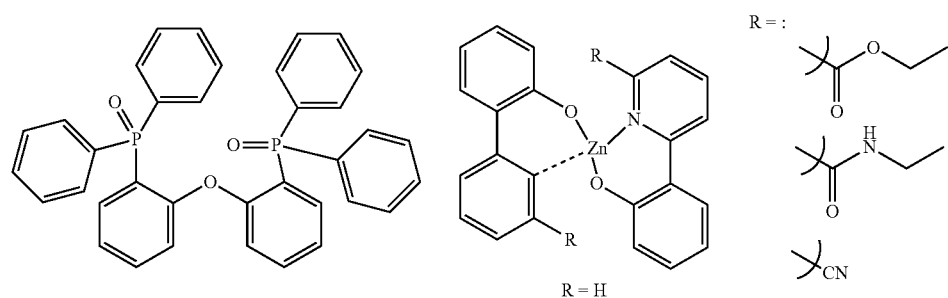
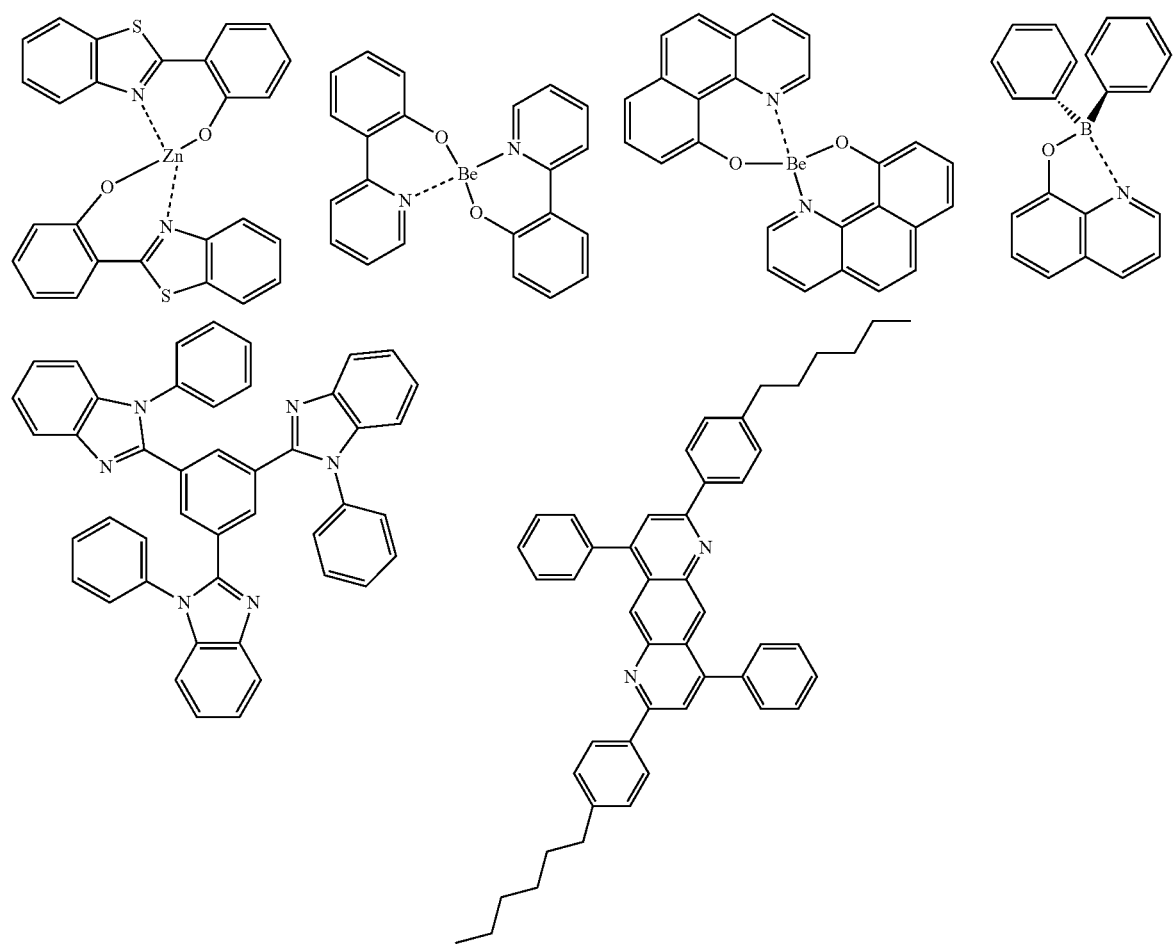

-continued
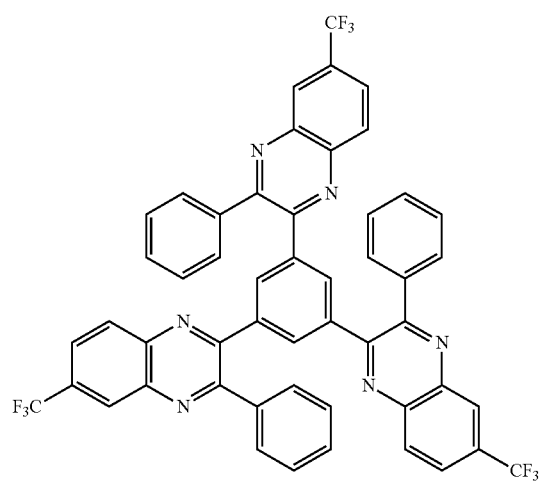
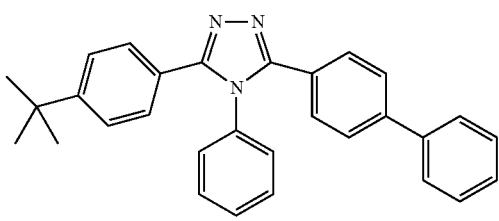
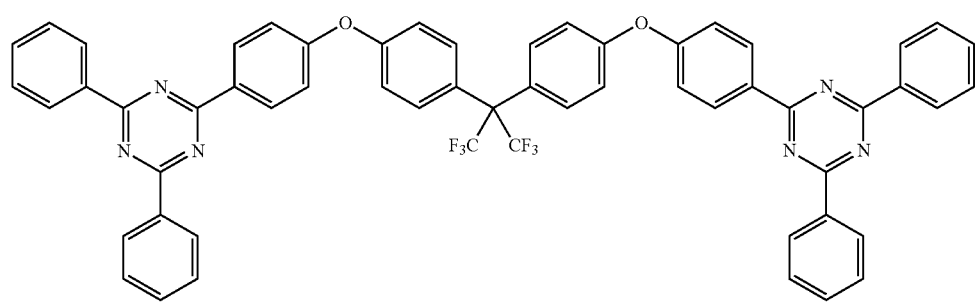
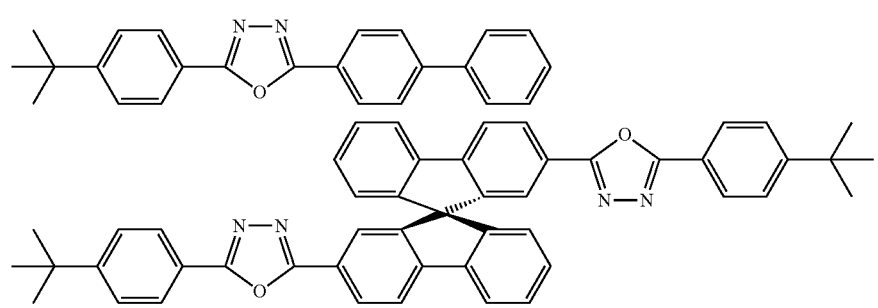
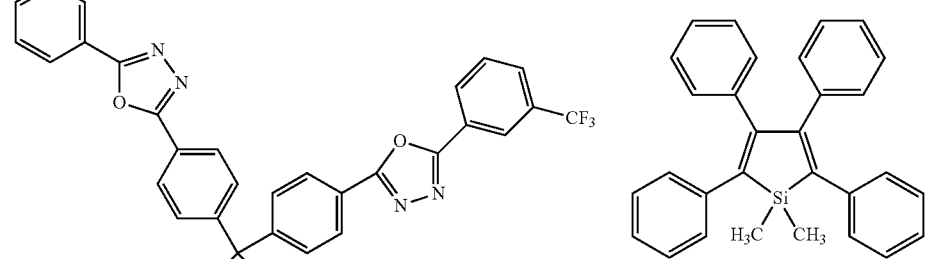
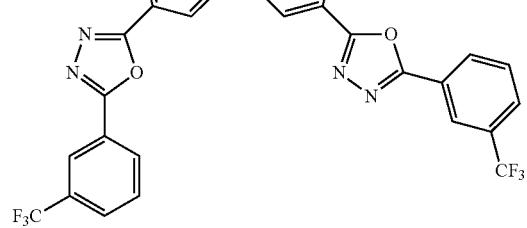

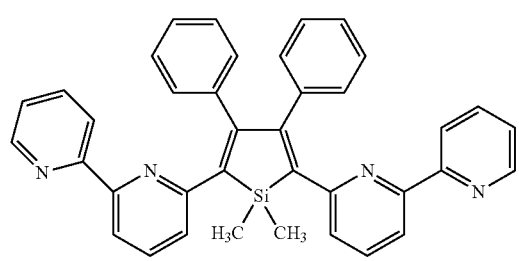
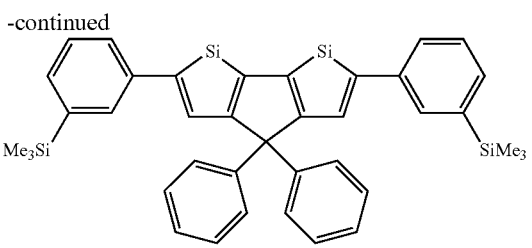
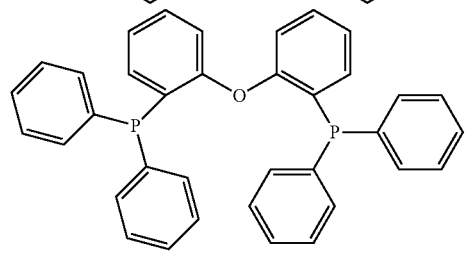
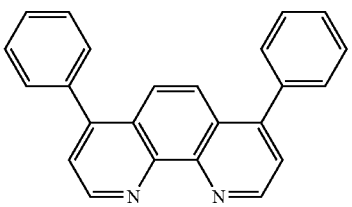
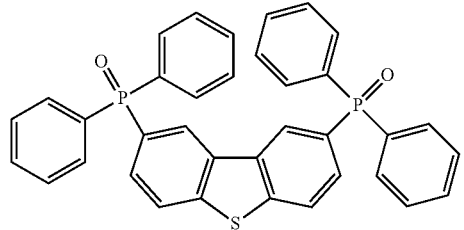
Preferred examples of a compound that may be used as the electron injection material are shown below.
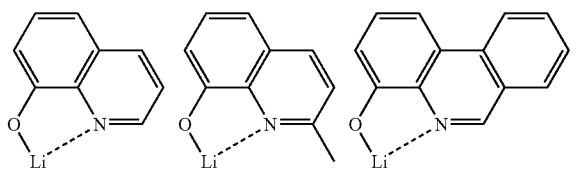
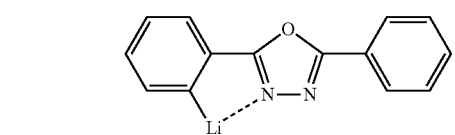
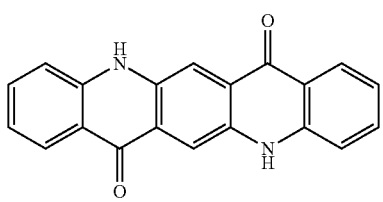
Preferred examples of a compound as a material that may be added are shown below. For example, the compound may be added as a stabilizing material.
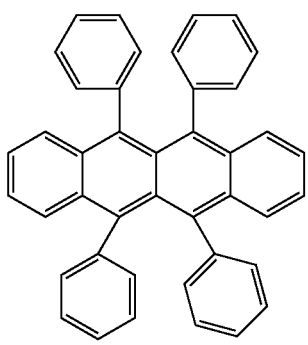
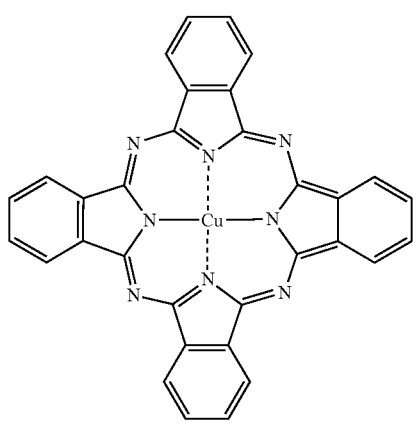

-continued

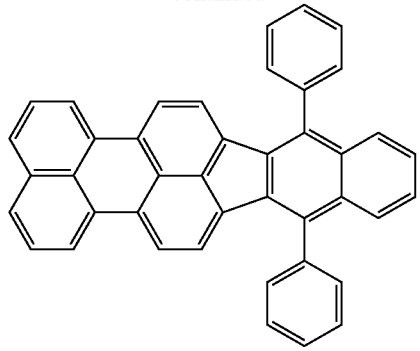

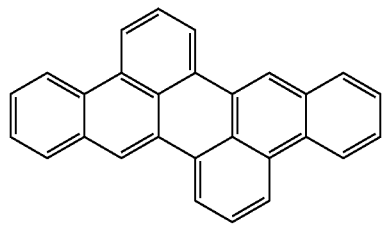

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat of the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a device having a structure with plural devices disposed in an array, and a device having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLE

The features of the invention will be described more specifically with reference to examples below. The materials, processes, procedures and the like shown below may be appropriately modified unless they deviate from the substance of the invention. Accordingly, the scope of the invention is not construed as being limited to the specific examples shown below.

Example 1

(1) Production of Organic Photoluminescent Device (Organic PL Device)

Figure 2:
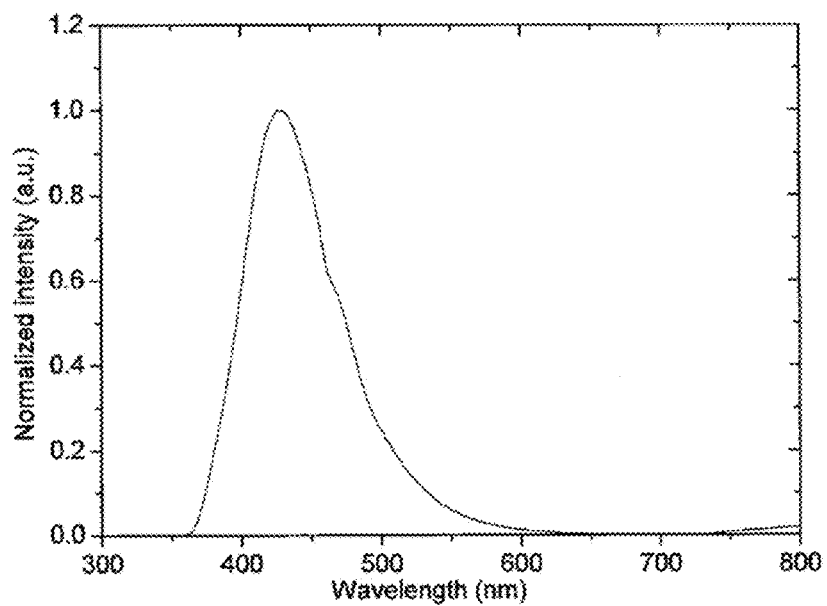
FIG. 2 is a photoluminescent light emission spectrum in Example 1.

6% by weight of the compound 1 and PYD2 were formed into a film on a quartz substrate by vapor co-deposition, and measured for PL light emission spectrum, PL quantum efficiency and PL transient decay. The PL light emission spectrum at an excitation wavelength of 337 nm is shown in FIG. 2. The vapor co-deposited film showed blue light emission and showed a high PL quantum efficiency of 32%.

Figure 3:
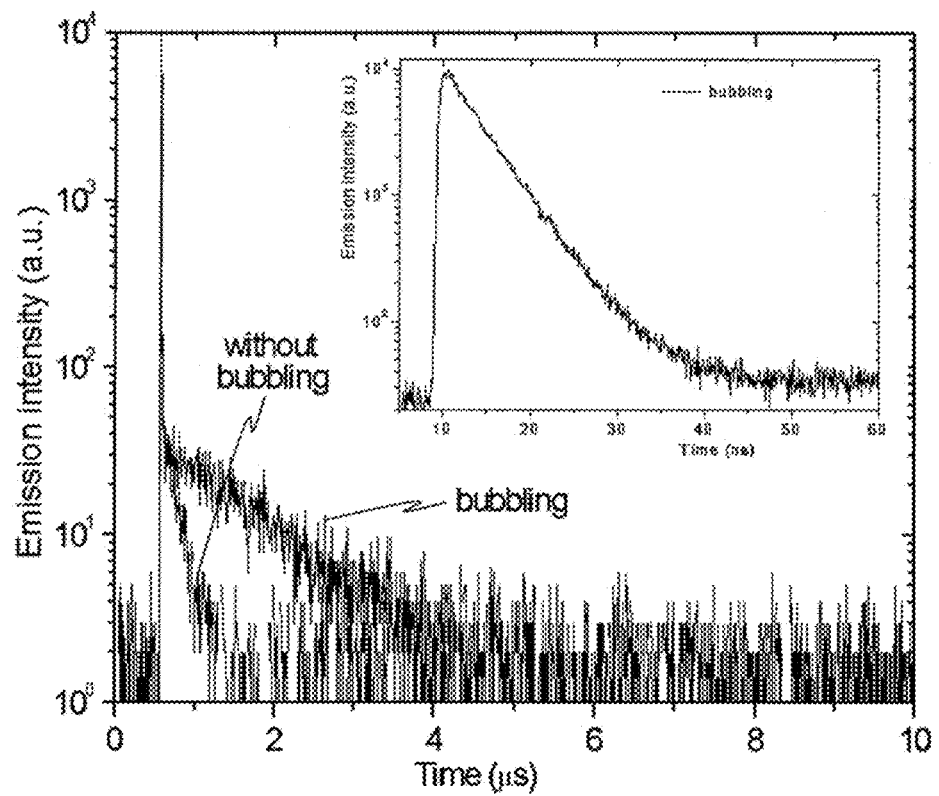
FIG. 3 is a graph showing a photoluminescent transient decay in Example 1.

For investigating the delayed fluorescence characteristics of the compound 1, the vapor co-deposited film was then measured for PL transient decay with a streak camera. The measurement result is shown in FIG. 3. The PL transient decay curve well agreed with the fitting of two components. In the measurement under bubbling with a nitrogen gas, a component having a short lifetime of 4 ns and a component having a long lifetime of 1.2 µs were observed, whereas in the measurement without a nitrogen gas bubbled, a component having a short lifetime of 5 ns and a component having a long lifetime of 256 ns were observed. Accordingly, delayed fluorescence derived from the long lifetime component was observed in addition to the fluorescent light with a short lifetime with the compound 1.

(2) Production of Organic Electroluminescent Device (Organic EL Device)

An organic electroluminescent device having the layer structure shown in FIG. 1 was produced in the following manner.

Figure 4:
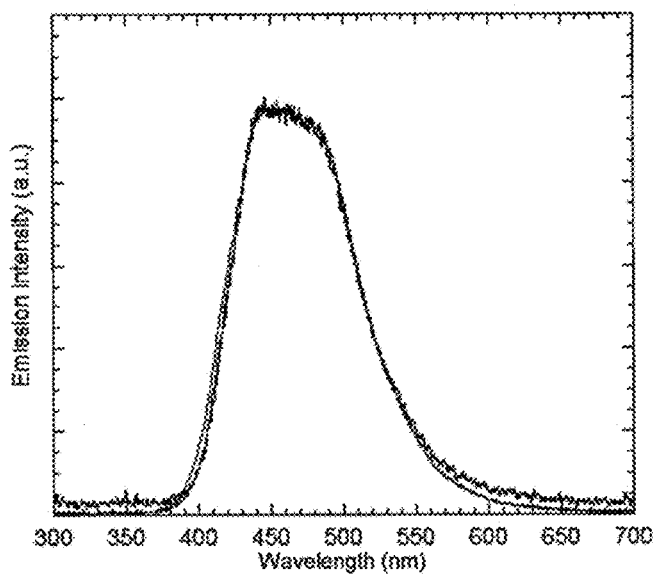
FIG. 4 is an electroluminescent light emission spectrum in Example 1.

Indium tin oxide (ITO) was formed into a film having a thickness of approximately from 30 to 100 nm on glass, and α-NPD was further formed into a film having a thickness of 60 nm thereon. Subsequently, 6% by weight of the compound 1 and PYD2 were formed into a film having a thickness of 20 nm by vapor co-deposition, which was designated as a light-emitting layer. Bphen was further formed into a film having a thickness of 40 nm thereon. Subsequently, magnesium-silver (MgAg) was vacuum vapor-deposited to a thickness of 100 nm, and then aluminum (Al) was vapor-deposited to a thickness of 20 nm, thereby completing an organic electroluminescent device having the layer structure shown in FIG. 1. The EL light emission spectrum of the organic EL device thus produced is shown in FIG. 4. The EL spectrum well agreed with the PL spectrum shown in FIG. 2, and thus it was confirmed that the light emission from the device was derived from the compound 1.

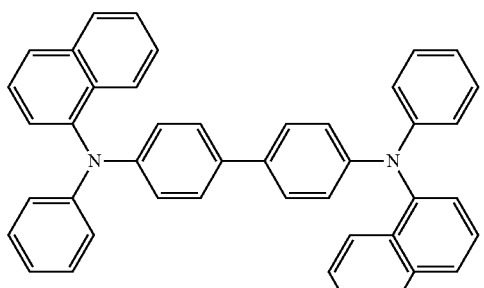

α-NPD

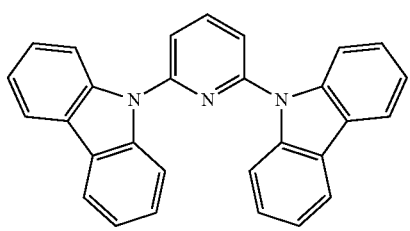

PDY2

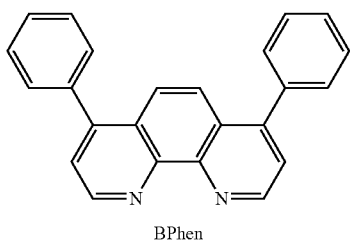

BPhen

Example 2

(1) Production of Organic Photoluminescent Device

Figure 5:
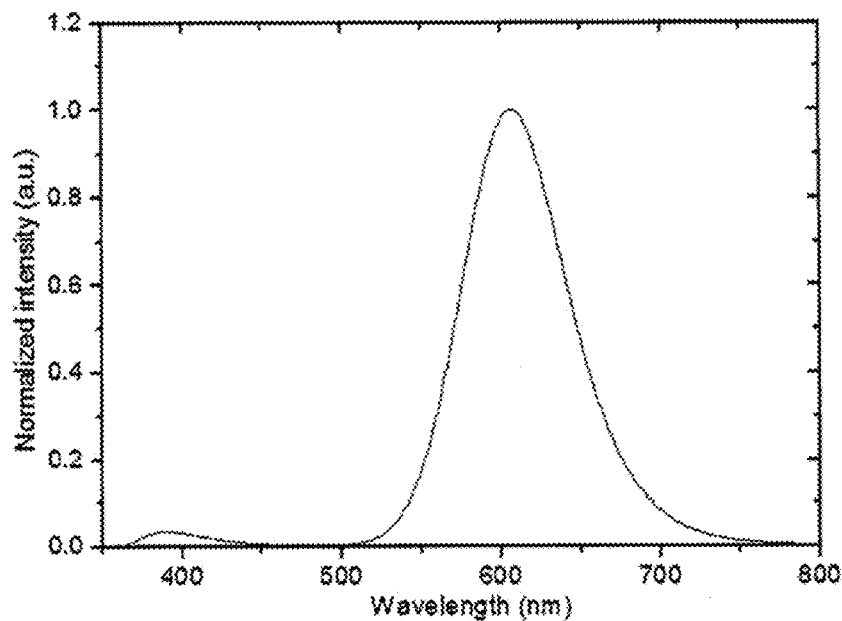
FIG. 5 is a photoluminescent light emission spectrum in Example 2.
Figure 6:
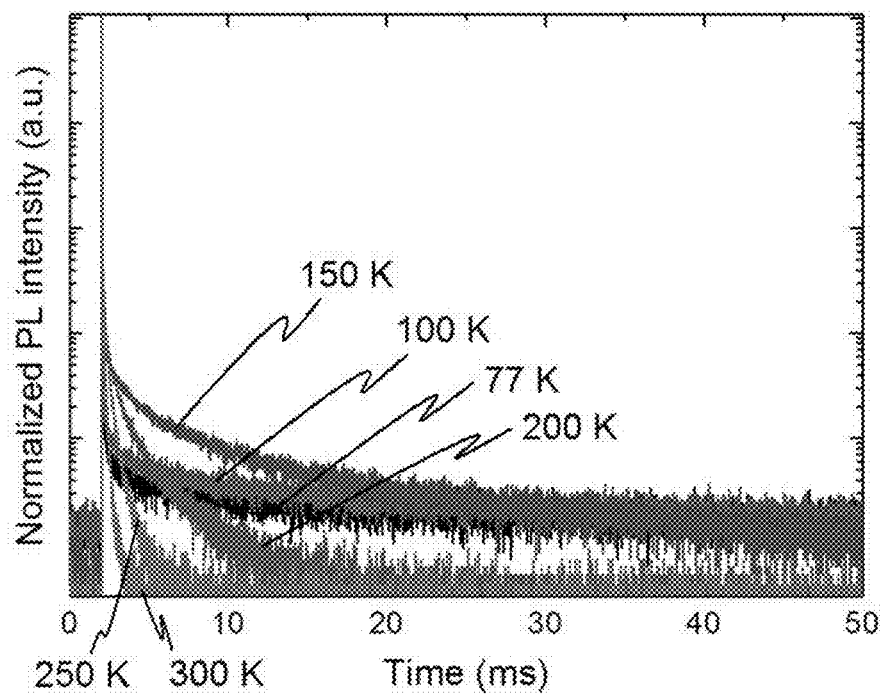
FIG. 6 is a graph showing a photoluminescent transient decay in Example 2.

6% by weight of the compound 101 and PYD2 were formed into a film on a quartz substrate by vapor co-deposition, and measured for PL light emission spectrum and PL quantum efficiency. The PL light emission spectrum at an excitation wavelength of 337 nm is shown in FIG. 5. The vapor co-deposited film showed red light emission and showed a high PL quantum efficiency of 91%. The results of the measurement of PL transient decay with a streak camera at 77 K, 100 K, 150 K, 200 K, 250 K and 300 K are shown in FIG. 6. It was confirmed from FIG. 6 that the delayed fluorescence depends on the temperature.

(2) Production of Organic Electroluminescent Device

An organic electroluminescent device having the layer structure shown in FIG. 1 was produced in the following manner.

Figure 7:
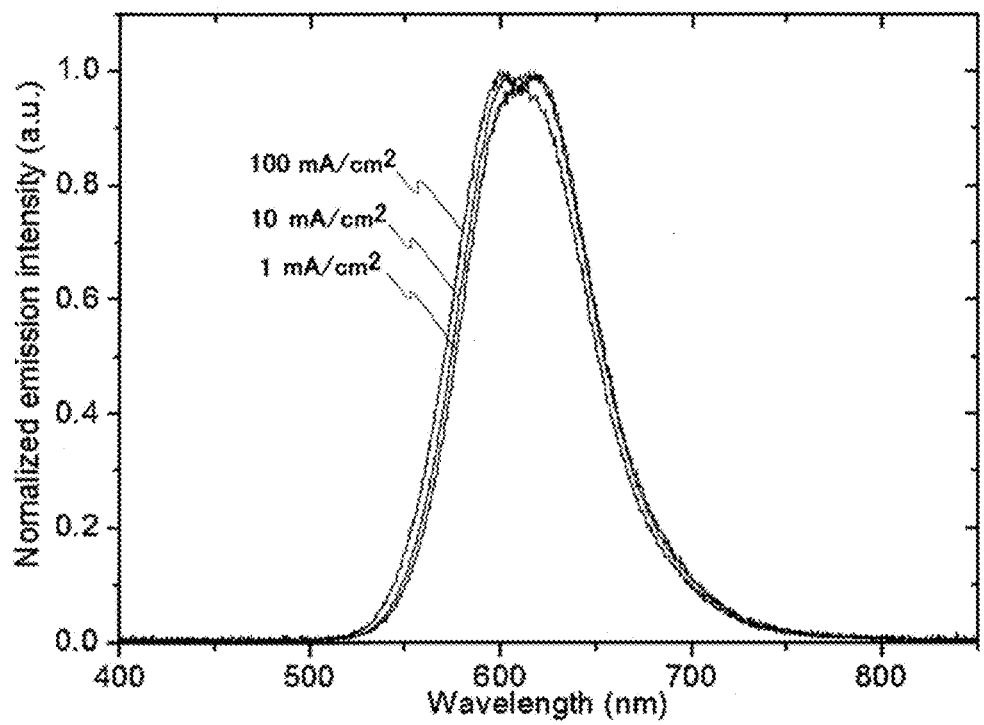
FIG. 7 is an electroluminescent light emission spectrum in Example 2.
Figure 8:
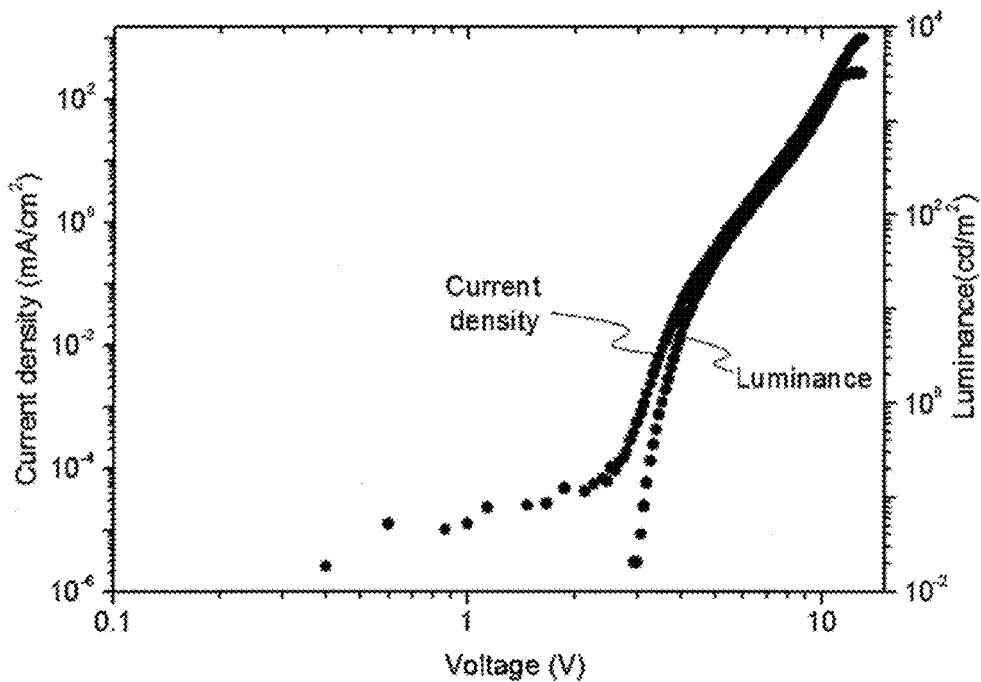
FIG. 8 is a graph showing electric current density-voltage characteristics-luminance characteristics of an organic electroluminescent device in Example 2.
Figure 9:
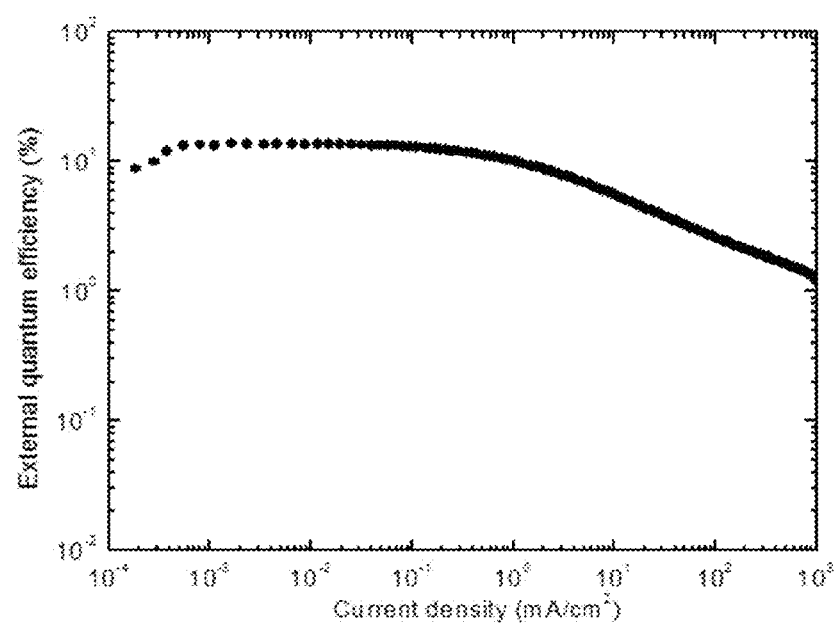
FIG. 9 is a graph showing external quantum efficiency-electric current density characteristics of the organic electroluminescent device in Example 2.

Indium tin oxide (ITO) was formed into a film having a thickness of approximately from 30 to 100 nm on glass, and α-NPD was further formed into a film having a thickness of 60 nm thereon. Subsequently, 6% by weight of the compound 101 and PYD2 were formed into a film having a thickness of 20 nm by vapor co-deposition, which was designated as a light-emitting layer. Bphen was further formed into a film having a thickness of 40 nm thereon. Subsequently, magnesium-silver (MgAg) was vapor-deposited to a thickness of 100 nm, and then aluminum (Al) was vapor-deposited to a thickness of 20 nm, thereby completing an organic electroluminescent device having the layer structure shown in FIG. 1. The electroluminescence (EL) spectrum is shown in FIG. 7. The EL spectrum well agreed with the PL spectrum, and thus it was confirmed that the light emission from the device was derived from the compound 101. The electric current density-voltage characteristics-luminance characteristics are shown in FIG. 8, and the external quantum efficiency-electric current density characteristics are shown in FIG. 9. It was confirmed that the external quantum efficiency was as high as 13.85%.

Example 3

The usefulness of the compounds 2 to 23 and the compounds 102 to 123 may be confirmed as similar to Examples 1 and 2.

INDUSTRIAL APPLICABILITY

The compound represented by the general formula (1) is useful as a light-emitting material of an organic light-emitting device. The compound represented by the general formula (1) includes one that exhibits emission of delayed fluorescent light and one that has an extremely high light emission efficiency. Accordingly, an organic light-emitting device using the compound represented by the general formula (1) as a light-emitting material exhibits emission of delayed fluorescent light and has an high light emission efficiency, and thus is significantly useful. Consequently, the invention has high industrial applicability.

REFERENCE SIGNS LIST 1 substrate
2 anode
3 hole injection layer
4 hole transporting layer
5 light-emitting layer
6 electron transporting layer
7 cathode

The invention claimed is:
1. A light-emitting material comprising a compound represented by the following formula (1):

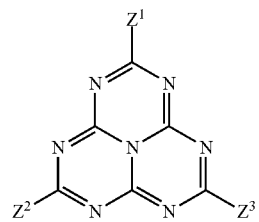

Formula (1)

wherein $Z^1$, $Z^2$ and $Z^3$ each independently represent an aryl group substituted by a substituted or unsubstituted diarylamino group.

2. The light-emitting material according to claim 1, wherein $Z^1$, $Z^2$ and $Z^3$ in the formula (1) are the same.

3. The light-emitting material according to claim 1, wherein the compound has a structure represented by the following formula (3):

Formula (3)

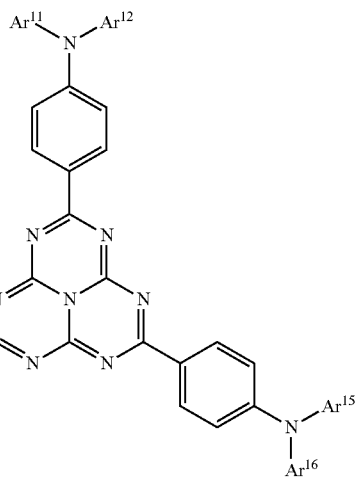

wherein $Ar^{11}$, $Ar^{12}$, $Ar^{13}$, $Ar^{14}$, $Ar^{15}$ and $Ar^{16}$ each independently represent a substituted or unsubstituted aryl group.

4. A delayed fluorescence emitter having a structure represented by the following formula (1):

Formula (1)

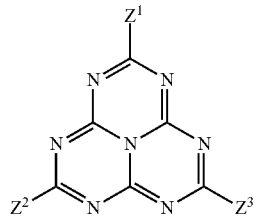

wherein $Z^1$, $Z^2$ and $Z^3$ each independently represent an aryl group substituted by a substituted or unsubstituted diarylamino group.

5. An organic light-emitting device comprising as a light-emitting material a compound represented by the following formula (1):

Formula (1)

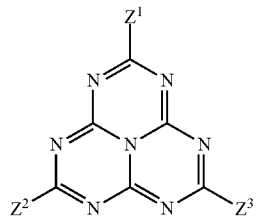

wherein $Z^1$, $Z^2$ and $Z^3$ each independently represent an aryl group substituted by a substituted or unsubstituted diarylamino group.

6. The organic light-emitting device according to claim 5, which is an organic electroluminescent device containing an anode, a cathode, and at least one organic layer containing a light-emitting layer between the anode and the cathode, and contains the light-emitting material in the light-emitting layer.

7. The organic light-emitting device according to claim 5, which emits delayed fluorescent light.

* * * * *